United States Patent
Zhang et al.

(10) Patent No.: US 10,064,698 B2
(45) Date of Patent: Sep. 4, 2018

(54) DENTAL DRILL HEAD

(71) Applicant: Zhengzhou Zezheng Technical Services Ltd., Zhengzhou, Henan (CN)

(72) Inventors: Chun Zhang, Henan (CN); Xiaoxia Liu, Henan (CN)

(73) Assignee: ZHENGZHOU ZEZHENG TECHNICAL SERVICES LTD., Zhengzhou, Henan (CN)

(*) Notice: Subject to any disclaimer, the term of this patent is extended or adjusted under 35 U.S.C. 154(b) by 0 days.

(21) Appl. No.: 13/685,214

(22) Filed: Nov. 26, 2012

(65) Prior Publication Data

US 2014/0038123 A1 Feb. 6, 2014

Related U.S. Application Data

(63) Continuation-in-part of application No. PCT/CN2012/082406, filed on Oct. 16, 2012, and a
(Continued)

(30) Foreign Application Priority Data

May 26, 2010 (WO) ............... PCT/CN2010/073256
Sep. 1, 2010 (CN) .......................... 2010 1 0268696
(Continued)

(51) Int. Cl.
*A61C 1/05* (2006.01)
*A61C 3/02* (2006.01)
(Continued)

(52) U.S. Cl.
CPC .............. *A61C 1/057* (2013.01); *A61C 1/052* (2013.01); *A61C 1/088* (2013.01); *A61C 3/02* (2013.01); *A61B 1/0684* (2013.01); *A61B 1/24* (2013.01)

(58) Field of Classification Search
CPC ................................ A61C 1/057; A61C 5/02
(Continued)

(56) References Cited

U.S. PATENT DOCUMENTS 2,895,738 A * 7/1959 Baker ............................ 279/53
3,578,872 A * 5/1971 McBurnie .......... A61B 17/1626
415/25
(Continued)

FOREIGN PATENT DOCUMENTS

CN 1306804 A 8/2001
CN 2510028 Y 9/2002
(Continued)

OTHER PUBLICATIONS

Machine Translation of EP0497139 A1. Accessed at EPO website on Apr. 6, 2016.*
(Continued)

*Primary Examiner* — Edward Moran
(74) *Attorney, Agent, or Firm* — Hamre, Schumann, Mueller & Larson, P.C.

(57) ABSTRACT

A dental drill head, constituted of a head housing, a wind wheel, and bearings, the head housing being constituted of a head housing cover and a head housing cavity, and the wind wheel being constituted of a wind wheel shaft and wind wheel blades. An anti-suck-back device is configured between the head housing cover and a wind wheel shaft end part to which the wind wheel shaft corresponds. The present invention, which adopts the aforementioned technical scheme, firstly makes it possible to reduce the intake in of contaminants when suck-back is taking place as the impeller is braked; and secondly, while there is still a positive pressure inside the head, the rubber head covering uses elastic force to brake the impeller and completely prevents the intake of contaminants. Moreover, the structure is simple (Continued)

and costs are low. Since the pressing area is reduced and the cavity is arranged between the rubber layers and the head covering, the teeth are less susceptible to touching the pressing portion. Even when the teeth do happen to touch the pressing portion, the cavity is so arranged that the teeth still will not touch the brake disc, thus avoiding any effect on the rotational speed; arranging the rubber ring inside the annular slot both prevents suck-back and automatically adjusts the dynamic balance, which is a double advantage and also lowers costs.

8 Claims, 24 Drawing Sheets

Related U.S. Application Data continuation-in-part of application No. PCT/CN2011/072262, filed on Mar. 29, 2011.

(30) Foreign Application Priority Data

| Sep. 7, 2010 | (CN) | 2010 2 0519642 U |
| Sep. 20, 2010 | (CN) | 2010 2 0536479 U |
| Sep. 27, 2010 | (CN) | 2010 2 0542727 U |
| Oct. 9, 2010 | (CN) | 2010 2 0554215 U |
| Oct. 25, 2010 | (CN) | 2010 2 0575024 U |
| Oct. 12, 2011 | (CN) | 2011 1 0324919 |
| May 26, 2012 | (CN) | 2012 1 0183800 |
| Sep. 14, 2012 | (CN) | 2012 1 0354925 |

(51) Int. Cl.
*A61C 1/08* (2006.01)
*A61B 1/24* (2006.01)
*A61B 1/06* (2006.01)

(58) Field of Classification Search
USPC ....... 433/29, 103–133; 415/904, 202, 25, 36
See application file for complete search history.

(56) References Cited

U.S. PATENT DOCUMENTS

| 4,341,520 A * | 7/1982 | Wallace | 433/132 |
| 5,334,013 A | 8/1994 | Meller | |
| 5,507,642 A * | 4/1996 | Wohlgemuth | 433/132 |
| 5,800,172 A | 9/1998 | Goldenberg | |
| 5,810,588 A | 9/1998 | Cohen | |
| 6,270,342 B1 | 8/2001 | Neuberger et al. | |
| 6,673,864 B2 * | 1/2004 | Patel et al. | 524/494 |
| 6,676,374 B2 * | 1/2004 | Hashimoto et al. | 415/202 |
| 7,261,561 B2 * | 8/2007 | Ruddle | A61C 1/07 433/122 |
| 7,303,394 B2 * | 12/2007 | Ma tre et al. | 433/129 |
| 7,329,123 B2 * | 2/2008 | Tanaka et al. | 433/132 |
| 2004/0126730 A1 * | 7/2004 | Panagotacos et al. | 433/29 |
| 2007/0121786 A1 * | 5/2007 | Okawa et al. | 378/119 |

FOREIGN PATENT DOCUMENTS

| CN | 2576198 Y | 10/2003 |
| CN | 1456129 A | 11/2003 |
| CN | 2596652 Y | 12/2003 |
| CN | 1887237 A | 1/2007 |
| CN | 200973753 Y | 11/2007 |
| CN | 100464111 C | 2/2009 |
| CN | 201333101 Y | 10/2009 |
| CN | 101658443 A | 3/2010 |
| CN | 201481569 U | 5/2010 |
| EP | 0192415 A1 | 8/1986 |
| EP | 0497139 A1 * | 8/1992 |
| JP | 60168807 | 11/1985 |
| JP | 1992050015 | 11/1992 |
| JP | 0970407 | 3/1997 |
| JP | 2003325546 A | 11/2003 |

OTHER PUBLICATIONS

International Search Report for Application No. PCT/CN2011/072262 dated Jul. 7, 2011.
International Written Opinion of the International Searching Authority for Application No. PCT/CN2011/072262 dated Jul. 7, 2011.
International Search Report for Application No. PCT/CN2010/073256 dated Sep. 2, 2010.
International Written Opinion of the International Searching Authority for Application No. PCT/CN2010/073256 dated Sep. 2, 2010.
Japanese Office Action for Application No. 2013-511514 dated Nov. 18, 2014.

* cited by examiner

DENTAL DRILL HEAD

CROSS-REFERENCE TO RELATED APPLICATIONS

The present application is a continuation-in-part of International Application No. PCT/CN2012/082406 filed Oct. 16, 2012, which claims priority from Chinese Patent Application No. 201110324919.2 filed Oct. 12, 2011 and Chinese Patent Application No. 201210183800.2 filed May 26, 2012; and is a continuation-in-part of International Application No. PCT/CN2011/072262 filed Mar. 29, 2011, published in Chinese, which claims priority from International Application No. PCT/CN2010/073256, filed May 26, 2010, Chinese Patent Application No. 201010268696.8 filed Sep. 1, 2010, Chinese Patent Application No. 201020519642.X filed Sep. 7, 2010, Chinese Patent Application No. 201020536479.8 filed Sep. 20, 2010, Chinese Patent Application No. 201020542727.X filed Sep. 27, 2010, Chinese Patent Application No. 201020554215.5 filed Oct. 9, 2010, and Chinese Patent Application No. 201020575024.7 filed Oct. 25, 2010, all of which are incorporated herein by reference.

FIELD OF TECHNOLOGY

The present invention relates to an important grinding tool used in dentistry—a head for a dental drill, in particular for a dental turbine drill.

BACKGROUND ART

In general, a head for an air-type cutting device used in dentistry is provided with a head part at the top thereof, the required components of a cutting tool being built into the head part, where the components comprise a rotor shaft of the cutting tool, two bearings rotatably supporting the shaft, and an impeller arranged between the two bearing parts; high-pressure air supplied via an air supply route arranged within a handle part of the head impacts the impeller to rotate the cutting tool. Conventional wind wheel shafts and blades for disposable dental drills are entirely composed of injection molded parts, such as in Chinese Patent No. 200520045733.3, in which a wind wheel shaft and bur act in concert through a three-piece spring, or Chinese Patent Application No. 200910001394.1, in which a bur hole of an wind wheel shaft is arranged so as to be in the shape of a spline and so as to clamp a bur shaft via a plastic elastic clip; also, in the aforementioned patent, a wind-resistant round piece is arranged, whereby the moment of inertia is increased. Other disposable dental drills utilize an interference fit between a bur hole and bur shaft or the like; such structures require a special tool to load and unload the bur, and this has proven inconvenient. Although Chinese Patent Application 201020542727.X is also for a push button dental drill it specifically comprises a wedge chuck within a wind wheel shaft, and the wedge chuck is used to clamp a bur. A connecting rod of the wedge chuck extends out of the wind wheel shaft and affixes a retaining board, while a disc spring is arranged between the retaining board and the wind wheel shaft on the outer periphery of the connecting rod, with a clamping force being provided by the disc spring. None of the above-described disposable dental drills has entered the stage of practical usage, for the reason that although China has several different factories producing disposable dental drills having an interference fit imparted by an wind wheel shaft and a bur, the general accuracy of molds in China is 0.04 to 0.06 mm, and the accuracy for injection molding components is even poorer; thus, in an environment of 300,000 revolutions per minute, the poor accuracy leads to imbalances, causing vibration noise, whereby standards are not met, and there is thus no practical use for these types of handpieces. The two above-described dental drills, in which pressure is used to load and unload the bur, have an even more complex structure, greater imbalance during rotation, and greater noise. Moreover, at present with repeat-usage metal dental drills, the price is directly dependent on the machining precision, and the highest prices amount to a hundredfold difference. Furthermore, since the head is to be extended into the oral cavity, a negative pressure is produced within the drill head when the supply of high-pressure air is discontinued and the impeller continues rotating with inertia at high speed, whereby external contaminants are drawn into the air supply route of the head; already, several anti-suck-back handpieces have appeared, but all of these prevent suck-back at the bur insertion site, which is a site with very little space, and thus the considerable precision required for the components used has led to a corresponding increase in cost. An LED light arranged at the front end of the handpiece has thus far been located on the neck of the handpiece; when the handpiece is used in this manner, the effectiveness of the illumination is not ideal, since the angle is problematic. When the LED light is arranged on the lowest part of the dental handpiece, the LED light and the switch are two separate elements and thus occupy too much space on the head; this makes installation difficult, and considerably increases the costs and difficulty of production.

DISCLOSURE OF THE INVENTION

It is an objective of the present invention to provide an anti-suck-back dental drill head with a simple structure and low costs. In order to resolve a problem in which a rubber cover of an anti-suck-back dental drill head touches the teeth, which has an effect on the rotational speed, a second objective of the present invention is to provide an anti-return-suction dental drill head whereby the rotational speed will not be affected even though the press cover may touch the teeth. A third objective is to resolve the problem of suck-back in the dental drill heads of the prior art and at the same time resolve the problem of dynamic balance during high speed rotation of the wind wheel. A fourth objective of the present invention is to provide an LED lamp assembly to be applied to a dental drill head, the assembly having a simple structure and being easy to install. A fifth objective of the present invention is to provide a dental turbine drill which is small in volume, can be installed onto a lower air outlet channel, and uses air flow as a power switch. A sixth objective of the present invention is to provide a turbine drill in which an elastic membrane is not a conductor or in which an elastic membrane does not affix a conductor. A seventh objective of the present invention is to obviate the need for a special air jet channel for atomized water vapor, and at the same time to do so without lowering atomization efficacy. An eighth objective of the present invention is to provide a handpiece which is thin-walled, sturdy, with a simple structure, and at the same time is still able to satisfy the needs of present and future usage.

In order to solve the aforementioned problems, the present invention employs the following technical scheme:

A dental drill head comprises: a head housing, a wind wheel, and bearings, the head housing being constituted of a head housing cover and a head housing cavity, and the wind wheel being constituted of a wind wheel shaft and wind wheel blades.

An anti-suck-back device is configured between the head housing cover and a wind wheel shaft end part to which the wind wheel shaft corresponds.

The head cover is a rubber head cover, and the periphery of the rubber head cover is affixed onto the head housing cavity.

The rubber head cover snaps onto a wind wheel shaft end surface of the wind wheel.

A brake disc is arranged at one end of the wind wheel shaft of the wind wheel that corresponds to the rubber head cover.

The shapes of the outer surface of the brake disc and the inner surface of the rubber head cover correspond to each other.

A brake disc keyhole that communicates directly to a wind wheel shaft hole of the wind wheel shaft is arranged at the center of the brake disc, and a rubber head cover keyhole is arranged on the rubber head cover so as to correspond to a center hole of the wind wheel shaft.

The fact that the brake disc is arranged at the end of the wind wheel shaft of the wind wheel that corresponds to the rubber head cover means that a bur clamping mechanism is arranged within the wind wheel shaft hole of the wind wheel, the bur clamping mechanism comprising a clamping jaw located on the inside of the wind wheel shaft hole, a clamping jaw rod that is coupled to the clamping jaw, and the brake disc, which is coupled to the top of the clamping jaw rod; a spring is fitted onto the clamping jaw rod between the brake disc and the top of the wind wheel shaft.

The clamping jaw rod and the wind wheel shaft hole engage in the manner of a sliding key.

A rubber piece is arranged between the head housing and the wind wheel; in the natural state, the rubber piece is in contact with both the head housing and the wind wheel at the same time, but in a working state, the rubber piece separates from either the head housing or the wind wheel.

The rubber piece refers to a rubber layer affixed to the inside of the head covering of the head housing; the rubber layer and the head covering together form the cavity, and in the natural state the rubber layer is in contact with the wind wheel shaft end part, while in the working state the rubber layer separates from the wind wheel shaft end part.

The head covering is provided with a vent hole, and the vent hole is linked to the cavity formed by the rubber layer and the head covering.

A rubber pocket is fixed to the inside of the head covering, the rubber pocket being provided with an air outlet hole and being linked to the vent hole; a portion of the rubber pocket not in contact with the head covering is a rubber layer.

The head covering is provided with a window, the periphery of the window being a window slot; an elastic expansion ring inside the rubber pocket fastens the periphery of the rubber pocket into the window slot of the periphery of the window of the head covering.

A retaining ring is arranged on the outside of the window slot of the head covering, and a retaining block is arranged between the retaining ring and the rubber pocket; in the working state, the retaining block stops the rubber pocket from bulging out of the head covering.

The wind wheel shaft end part is provided with a brake disc.

The wind wheel shaft end part is provided with a second brake disc, whereby a brake disc II is arranged on a spring retaining ring; an annular slot I is provided on the brake disc II, and a rubber ring I is arranged within the annular slot I. In the natural state, the rubber ring I is in contact with the head covering, but in the working state the rubber ring I separates from the head covering into the slot due to centrifugal force.

A rubber membrane is provided on the rubber ring I.

An annular slot II is provided to a wind wheel blade side of the wind wheel shaft, and a rubber ring II is arranged within the annular slot II; in the natural state, the rubber ring II is in contact with a bearing seat of the head housing, but in the working state, the rubber ring II separates from the bearing seat into the slot due to centrifugal force.

An LED assembly arranged on the dental drill head has an LED lamp with an annular shape, the upper surface thereof being an electrode; an electroconductive film supported by an insulator is provided on the upper surface of the annular LED lamp. The contact and separation between the electroconductive film and the upper surface of the annular LED lamp constitutes an LED lamp switch, and the LED lamp assembly is fixed onto the head casing and arranged so as to surround the bur.

The electroconductive film is a metallic film.

The electroconductive film is a non-metallic film that has been coated with an electroconductive adhesive.

The non-metallic film is electroconductive polyester or polyvinylchloride.

A dental turbine drill provided with a dental drill head comprises a handle and a head that is connected to the handle, the head being constituted of a head housing and a core that is arranged within a cavity of the head housing, and the head housing being constituted of a head housing wall and a head housing covering, the core being constituted of a connecting shaft turbine and an upper bearing and a lower bearing that are fitted at corresponding upper and lower sites on a turbine shaft of the connecting shaft turbine, the upper bearing and the lower bearing being placed onto corresponding bearing seats inside the head housing, the dental turbine drill being characterized by a turbine cavity formed between the upper bearing and the lower bearing, the turbine cavity being provided with an air supply channel and an air return channel, an upper part of the upper bearing seat is an upper air outlet channel and a lower part of the lower bearing seat is a lower air outlet channel; the site of the connection between the handle and the head housing is a handle neck, both the head housing and the handle being made of a plastic material.

An LED surface mount lamp is arranged on the outer periphery of a bur socket on the outside of the head housing wall, and the LED surface mount lamp is connected to a power source and a switch, the switch referring to a pneumatic membrane switch provided on the lower air outlet channel.

The pneumatic membrane switch is constituted of two membrane rings that are isolated from an annular isolation layer I by a distance that corresponds to the annular isolation layer I, projecting blades being arranged in the direction of the ring center of the two membrane rings, where the pneumatic membrane switch is configured to open and close by the contact and separation of the two corresponding projecting blades.

An annular one-way valve is fixed onto the air outlet channels, the annular one-way valve being an annular stretched elastic membrane. In the natural state, a center hole of the annular stretched elastic membrane holds onto the turbine shaft or holds onto the bur, and in the working state, the center hole of the annular stretched elastic membrane is blown away from the turbine shaft or is blown away from the bur. In the natural state, a portion of the lower surface of the annular stretched elastic membrane separates from the internal parts of the head, and in an air expelling state, that portion is in contact with the internal parts of the head, whereby the site of contact between the inside of the head and that portion of the lower surface of the annular stretched elastic membrane constitutes a switch.

An annular pressure membrane switch is arranged under the annular stretched elastic membrane; the annular pressure membrane switch constitutes at least two isolated points arranged between an upper elastic ring and a lower elastic ring; the sites where there is not an isolated point are in pressurized contact, so that there is separation in the natural state, whereby a pressure membrane switch is constituted.

The power source is a button battery or a pin type battery arranged on one side of the neck of the head.

The turbine drill is a push button turbine drill, the material of the head covering is a rubber-like substance, and the head covering of the rubber-like substance is tightly clamped by a collar against an upper part of the head housing wall.

The head covering of the rubber-like substance is a silicon rubber, polyurethane, latex, or an ordinary rubber.

The turbine drill is a push button turbine drill, in which a bur pressure clamping mechanism is a tapered hole arranged on the center hole of the turbine shaft, a clamping jaw being provided within the center hole of the turbine shaft, where the clamping jaw has a wedge shape along the axial direction of the turbine shaft that is mated to the tapered hole; an upper part of the clamping jaw is integrally fixed to a connecting rod and an upper part of the connecting rod extends out of the center hole of the turbine shaft and is integrally fixed to a spring retaining plate. A spring is provided between the turbine shaft and the elastic retaining plate on the outside of the connecting rod; the turbine shaft, the clamping jaw, the connecting rod, and the elastic spring are all plastic pieces.

The spring is a butterfly spring or a leaf spring.

The butterfly spring or the leaf spring is arranged so as to have a relative snap superposition.

The present invention, which adopts the aforementioned technical scheme, firstly, makes it possible to reduce the intake of contaminants when suck-back is taking place as the impeller is braked; and secondly, while there is still a positive pressure inside the head, the rubber head covering uses elastic force to brake the impeller and completely prevents the intake of contaminants. Moreover, the structure is simple and costs are low.

Since the pressing area is reduced and the cavity is arranged between the rubber layers and the head covering, the teeth are less susceptible to touching the pressing portion. Even when the teeth do happen to touch the pressing portion, the cavity is so arranged that the teeth still will not touch the brake disc, thus avoiding any effect on the rotational speed; arranging the rubber ring inside the annular slot both prevents suck-back and automatically adjusts the dynamic balance, which is a double advantage and also lowers costs.

The structure is simplified by integrating the LED lamp with the switch for the LED lamp, and accordingly when the present invention is installed in a dental drill handpiece head, it will occupy comparatively less space in the head, and the installation itself will be easier.

The present invention also offers the following advances:

(1) The described films can be polyester (PET), polyvinyl chloride (PVC), or polysulfide acetate or the like. Such films are very thin, generally about 10 filaments, or 100 microns, enabling a very thin switch. The thickness of the LED surface mounting piece is also not large. This makes it possible to implement switching under circumstances whereby the size of the head is minimally increased, and to arrange the lamps uniformly on the head.

(2) By employing the annular stretched elastic membrane, which can not only act as a washer but also can prevent suck-back, the present invention makes it possible to maintain the original size of the dental drill, without an increase in volume, since only the original washer position is occupied.

(3) By using a membrane switch, the present invention makes possible an anti-return-air membrane on the air outlet channel that is simultaneously a membrane switch component, thus achieving the purpose of preventing suck-back while still occupying only a small volume.

(4) To make an electroconductive elastic membrane, adding silver powder to rubber is very costly, while adding carbon powder reduces elasticity; therefore a scheme in which an elastic membrane is used to package an electroconductive material to serve as a push button key requires a complex process and results in a somewhat greater volume. However, using the elastic membrane as the pressing force of the pressure membrane switch is a simple process with low cost that uses little space and meets requirements.

(5) In the present invention, the power source, or a portion of the power source, the switch, and the lamp are all disposed within the head, thus achieving the three objectives of compactness, connectedness, and low volume usage.

(6) By using rubber for the push button, the present invention makes it possible to forego a spring and other sealing members, and thus the structure is simple and costs are low.

(7) mm inner diameter bearings are used for the bearings in the present invention, and this leads to a corresponding increase in the mass of the rotating members as well as an improvement in the ability to operate smoothly. Rubber is used as the component material for the pressing mechanism corresponding to the bearings, and this makes it possible to achieve the requirements for subjected force and also resolve the technical problems of a low-cost pressing mechanism, for which a solution has long been sought. The use of a butterfly spring or a leaf spring makes it possible to drastically reduce spring costs, and having the spring retaining board serve as an inertia disc also improves the ability to operate smoothly.

(8) Having the atomized water vapor spray on both the upper air outlet channel and the lower air outlet channel in the present invention and having a large amount of rotational air flow through such areas makes it possible to achieve even more effective water vapor atomization.

(9) Using a grid support in the handle of the present invention allows for the handle wall to be thin yet sturdy. At the same time, having the grid channels simultaneously serve as dental drill functional channels achieves a dual usage with a single component, and thus allows for a simple structure.

With consideration given to all of the aforementioned advantages, provided is a disposable push button dental turbine drill that is practical, inexpensive, prevents suck-back with a simple process, and is self-illuminating. Also advantageous is the use of inexpensive parts.

MODES FOR CARRYING OUT THE INVENTION

Figure 1:
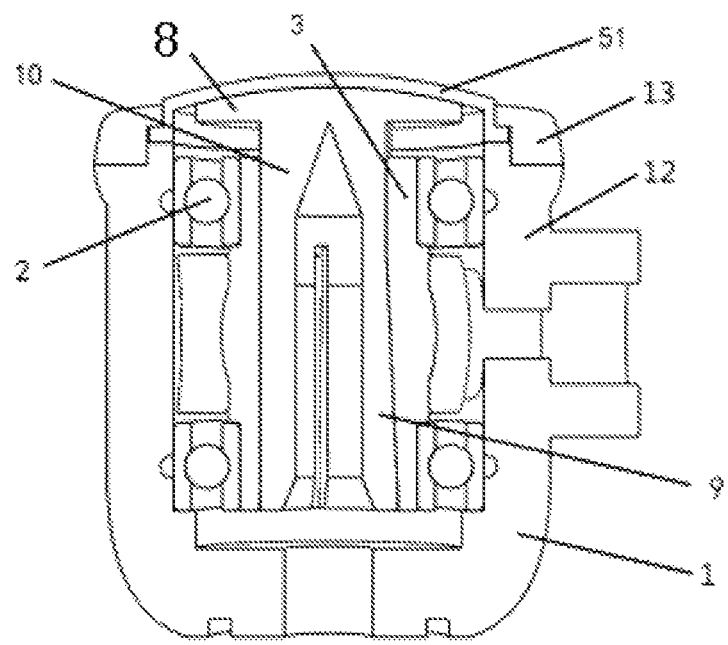
FIG. 1 is a schematic cutaway structural view of the natural state of the push button head.
Figure 2:
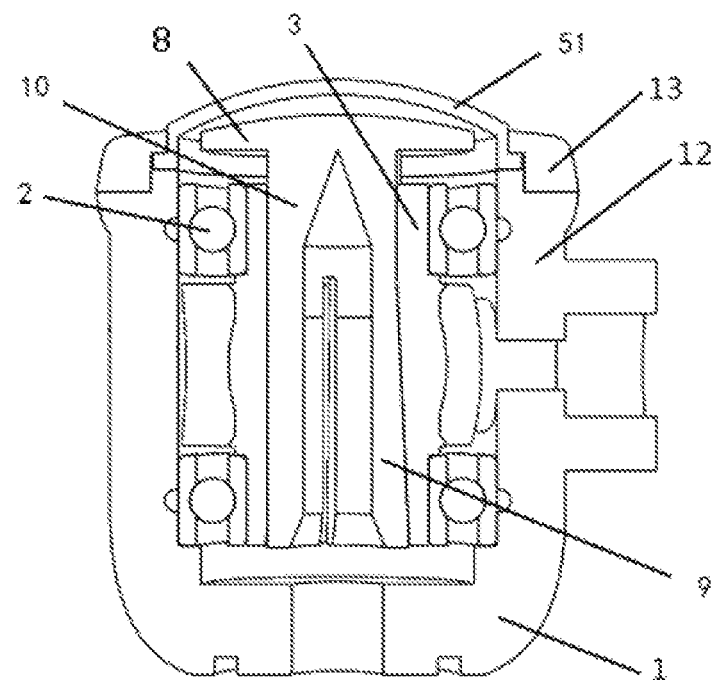
FIG. 2 is a schematic cutaway structural view of a positive pressure state within the push button head.

As illustrated in FIG. 1, an anti-suck-back dental drill head is constituted of a head housing 1, a wind wheel, and bearings 2, wherein a head covering of the head housing 1 is a rubber head covering 51, and a threaded ring 13 is used to screw the periphery of the rubber head covering 51 onto a head housing cavity 12. Combined with the view of FIG. 3, a bur clamping mechanism is arranged within a hole of a wind wheel shaft 3 of the wind wheel, the bur clamping mechanism comprising a clamping jaw 9 located within the hole of the turbine shaft, a clamping jaw rod 10 connected to the clamping jaw, and a brake disc 8 connected to a top part of the clamping jaw rod; a spring 28 is fitted onto the clamping jaw rod 10 between the brake disc 8 and the top part of the wind wheel shaft 3. FIGS. 1 and 2 depict the spring 28, and FIG. 3 includes a handpiece in which there is a butterfly spring, the spring being used by the clamping jaws to clamp the bur, at which time a push button is used to load or unload the bur.

The clamping jaw rod 10 is provided with a key 23, the hole of the wind wheel shaft is provided with a key groove 24, and the key 23 is fitted so as to slide into the key groove 24. This sliding key fit signifies that the shapes of the key 23 and of the key groove 24 are enable a spline fit, but the clamping jaw rod is able to move along the axis of the hole of the wind wheel shaft, causing the clamping jaw rod to rotate synchronously with the wind wheel shaft.

When rubber head covering 51 is not snapped onto the upper surface of the brake disc 8, and when the supply of high-pressure air is discontinued, an impeller will continue to rotate at high speed due to inertia, which creates negative pressure inside the head causing the rubber head covering to be sucked onto a wind wheel shaft end surface of the wind wheel; the two parts generate friction and stop the rotation of the wind wheel, thus decreasing the intake of contaminants.

When the rubber head covering 51 is snapped onto the upper surface of the brake disc 8, and when the high-pressure air is supplied, as is illustrated in FIG. 2, the positive pressure of the high-pressure air inside of the head causes the rubber head covering to rise and separate, losing contact with the end surface of the wind wheel shaft of the wind wheel, and also causes the impeller to rotate at high speed; when the supply of high-pressure air is discontinued, the impeller will continue to rotate at high speed due to inertia, which creates negative pressure inside the head and can cause the rubber head covering to clamp by elastic force onto the wind wheel shaft end surface of the wind wheel, thus stopping the rotation of the impeller and entirely preventing the intake of contaminants.

The upper surface of the brake disc 8 is shaped to mate to an inner surface of the rubber head covering 51. At this time, the force of friction created when the brake disc and the rubber head covering are entirely in contact with each other is even greater, thus causing the impeller to be even more readily stopped from rotating.

The above description is an example where the brake disc 8 is provided; when no brake disc 8 is provided, the handpiece is one in which a key is used to load and unload the bur, and not a handpiece in which a push button is used to load and unload the bur. The rubber head covering 51 acts as a brake on the upper end surface of the wind wheel shaft 3 of the wind wheel, the effect of which is not as favorable as when the brake disc 8 is provided, but this too is one mode of carrying out the present invention. When the rubber head covering 51 is not snapped onto the upper end surface of the wind wheel shaft 3 of the wind wheel, trace amounts of contaminants will be taken in, but when the rubber head covering 51 is snapped onto the upper end surface of the wind wheel shaft 3 of the wind wheel, it is also possible to entirely prevent the intake of contaminants, however the effect thereof is not as favorable as when the brake disc 8 is provided. In order to be able to replace the bur, a brake disc key hole that communicates directly with the wind wheel shaft hole of the wind wheel shaft is arranged at the center of the brake disc 8, and a rubber head covering key hole is arranged on the rubber head covering 51 so as to correspond with the center hole of the wind wheel shaft. The described handpiece lacks a bur clamping mechanism, and thus the brake disc 8 is fixed onto the upper end surface of the wind wheel shaft 3, similarly making it possible to prevent suck-back.

Figure 4:
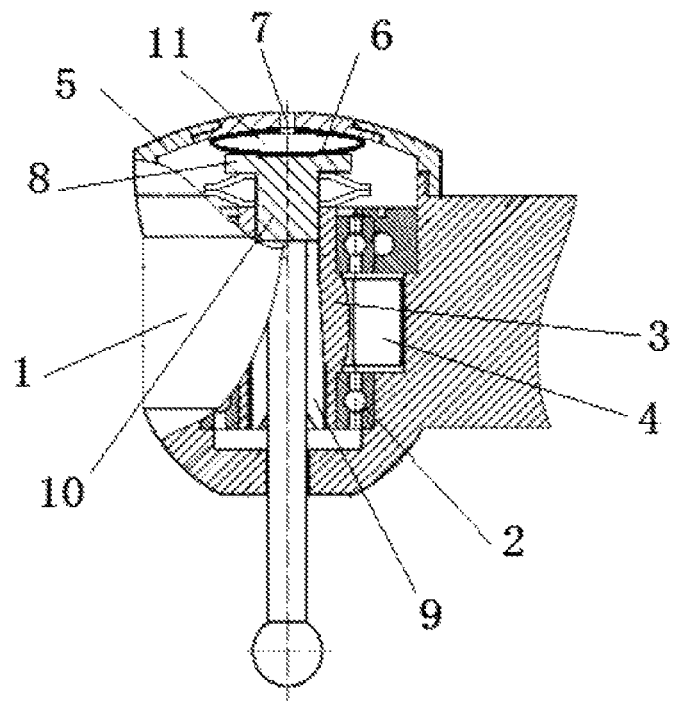
FIG. 4 is a schematic structural view of the natural state when the rubber pocket is fixed to this inside of the push button covering.
Figure 5:
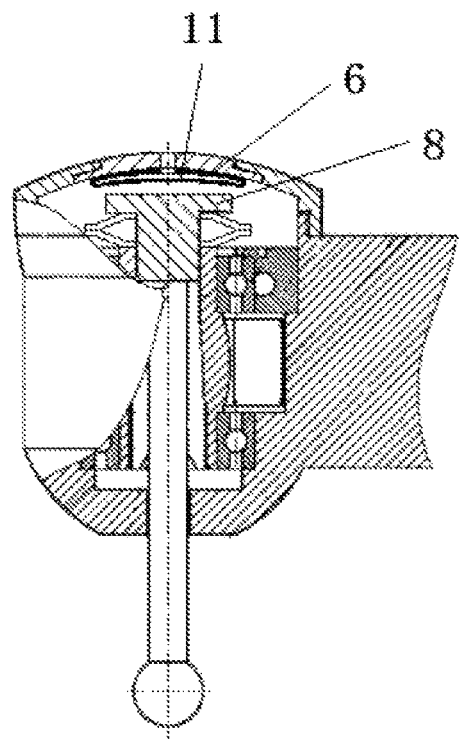
FIG. 5 is a schematic structural view of the operating state when the rubber pocket is fixed to the inside of the push button covering.

As is illustrated in FIGS. 4 and 5, a dental drill head is constituted of the head housing 1, the wind wheel, and the bearings 2, the wind wheel comprising the wind wheel shaft 3 and also wind wheel blades 4; a rubber piece is arranged between the head housing 1 and the wind wheel. In the natural state, the rubber piece is in contact with both the head housing 1 and the wind wheel at the same time, but in the operating state, the rubber piece separates from either the head housing 1 or the wind wheel. In the operating state, high-pressure air enters into the head and the high-pressure air pushes on the wind wheel and causes same to rotate, while the rubber piece separates from either the head housing or the wind wheel, allowing the wind wheel to rotate at high speed; when operation is stopped, the supply of the high-pressure gas is stopped, and the rubber piece is in contact with both the head housing and the wind wheel at the same time, thus braking the wind wheel and causing same to stop rotating, which has the effect of preventing the intake of contaminants.

Figure 3:
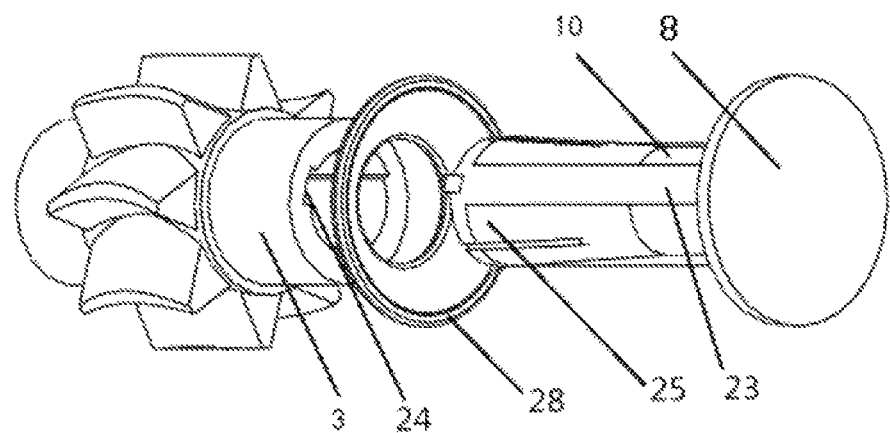
FIG. 3 is a view illustrating the assembly of a bur clamping mechanism.

The rubber piece is a rubber layer 6 affixed to the inside of the head covering 5 of the head housing 1, and the rubber layer 6 together with the head covering 5 forms a cavity. In the natural state, the rubber layer and the end part of the wind wheel shaft are in contact, as is illustrated in FIG. 1, and in the operating state, the rubber layer 6 is subjected to the air pressure inside of the head housing and separates from the end portion of the wind wheel shaft, as is illustrated in FIG. 2. When operation is stopped, the supply of high-pressure air is stopped, and the rubber layer returns to contacting the end part of the wind wheel shaft, as is illustrated in FIG. 1, thus braking the wind wheel and causing same to stop rotating, which has the effect of preventing the suck-back of contaminants. Since the inside of the cavity is at ambient air pressure, the inside of the head will be at positive pressure during the operating state, and the compression of air inside the cavity will cause the rubber layer 6 to separate from the end portion of the wind wheel shaft; during the natural state, the rubber layer returns to contacting the end part of the wind wheel shaft, as is illustrated in FIG. 1. In FIG. 3, the rubber layer is a rubber pocket 11, but it would also be possible for the periphery of a layer of rubber to be fixed to the inside of the head housing, which could be done by bonding or by a card/slot snap fixation method.

The head covering 5 is provided with a through hole 7, and the through hole 7 communicates with the cavity formed by the rubber layer 6 and the head covering 5. The cavity formed by the rubber layer 6 and the head covering 5 communicates with the outside air, which during the operating state assists the rubber layer to separate from the end portion of the wind wheel shaft. During the operating state, the positive pressure inside the head compels the air inside of the cavity to be expelled via the through hole 7, while in the natural state, the rubber layer returns to being in contact with the end part of the wind wheel shaft, as is illustrated in FIG. 1.

Figure 6:
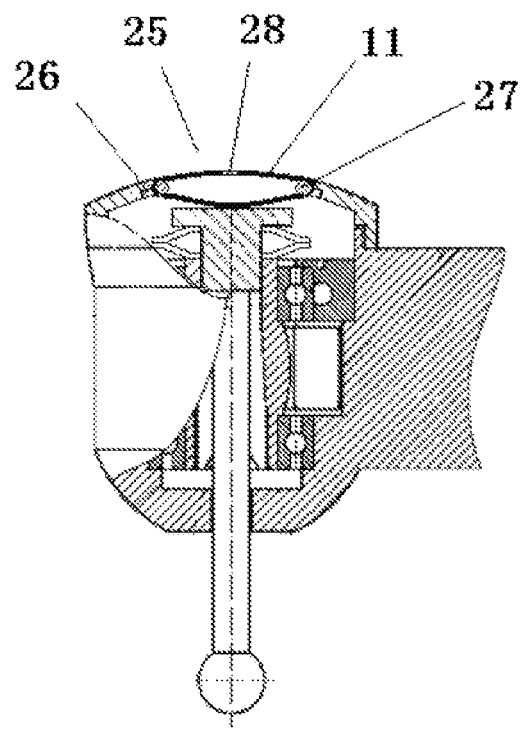
FIG. 6 is a schematic structural view of the natural state of the window provided to the head covering.

As is depicted in FIG. 6, the rubber pocket 11 is affixed inside the head covering 5, and the rubber pocket 11 is provided with a vent hole 7 to which an air outlet hole 28 communicates; the portion of the rubber pocket 11 not in contact with the head covering 5 is the rubber layer. The fixation of the rubber pocket 11 to the head covering 5 can be achieved simply by fixing one point between the rubber pocket 11 and the head covering 5, for example with bonding fixation.

Figure 7:
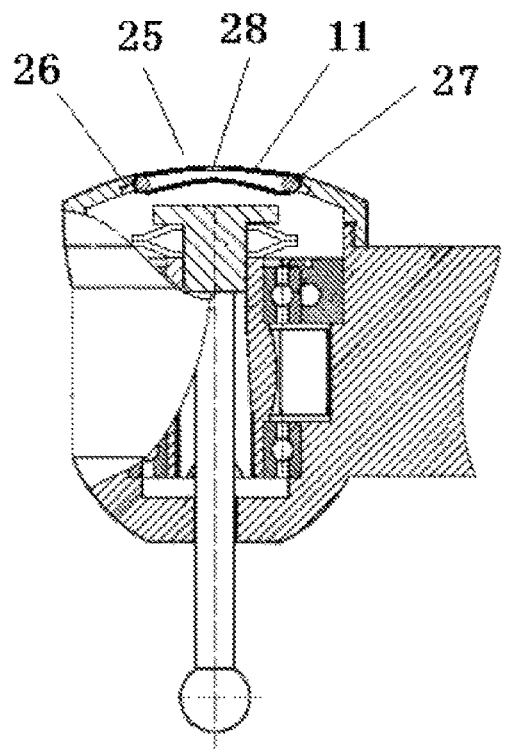
FIG. 7 is a schematic structural view of the operating state of the window provided to the head covering.

As is depicted in FIGS. 6 and 7, the head covering 5 is provided with a window 25, the periphery of the window 25 being a window slot 26. An elastic expansion ring 27 divides the rubber pocket into two surfaces, one surface serving as a portion of the head covering 5 and the other surface serving as the rubber layer 6.

Figure 8:
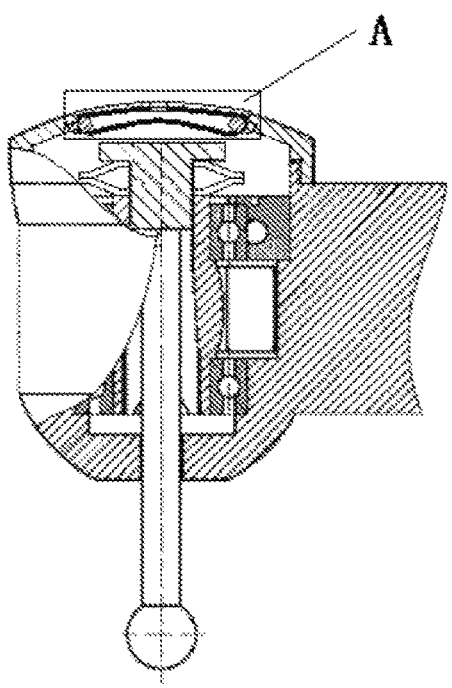
FIG. 8 is a schematic structural view of the retaining block provided to the window provided to the head covering.
Figure 9:
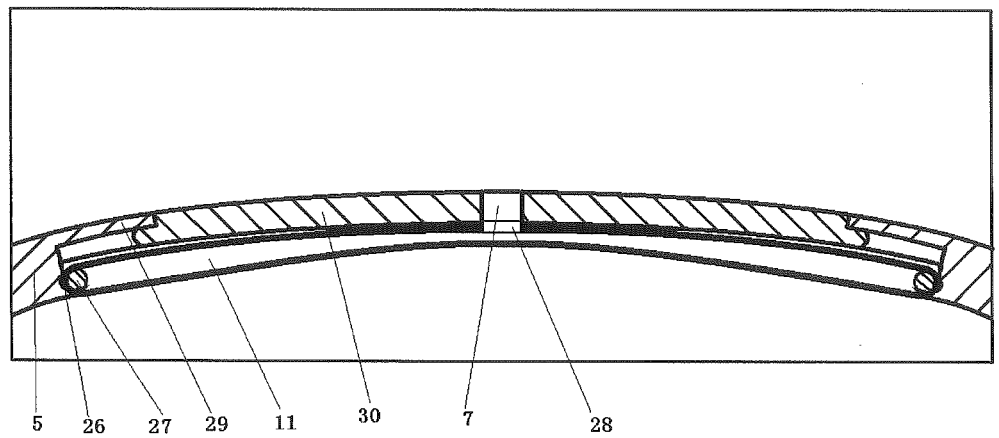
FIG. 9 is an enlarged view of a portion "A" in FIG. 5.

As is depicted in FIGS. 8 and 9, a retaining ring 29 is arranged on the outside of the window slot of the head covering, and a retaining block 30 is arranged between the retaining ring 29 and the rubber pocket 11; in the working state, the retaining block 30 prevents the rubber pocket 11 from bulging out of the head covering 5, but in the natural state, the retaining block 30 can be pressed inside the head.

The end part of the wind wheel shaft 3 is provided with the brake disc 8. Since the contact surface where the brake disc 8 and the rubber layer 6 are in contact with each other has a large surface area, it is conducive for braking the wind wheel to stop same from rotating.

Figure 10:
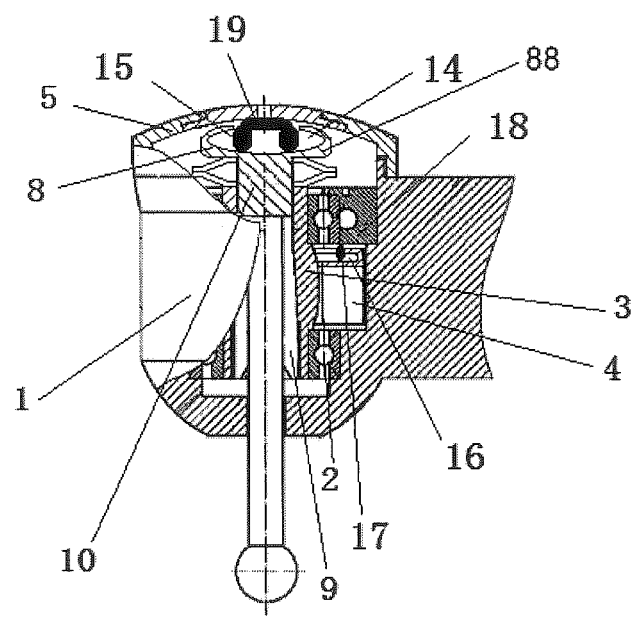
FIG. 10 is a schematic structural view of the natural state of the annular slot provided to the brake disc.
Figure 11:
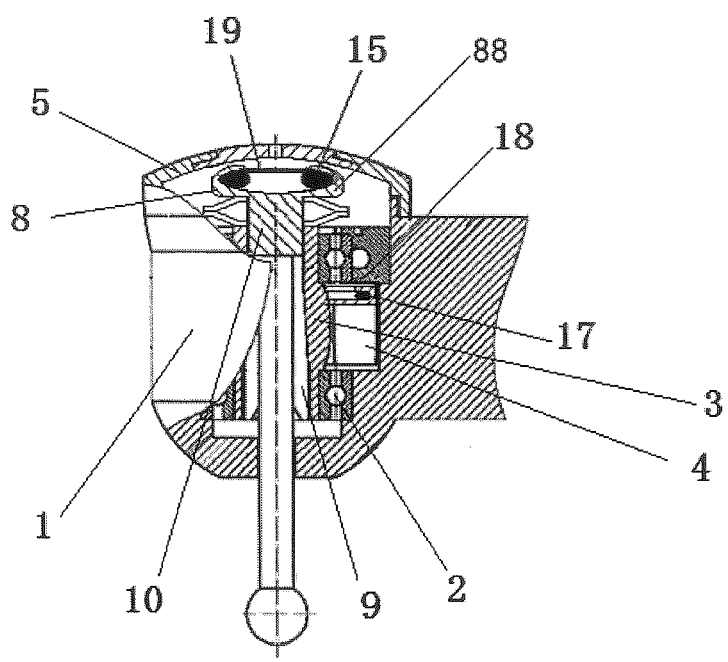
FIG. 11 is a schematic structural view of the operating state of the annular slot provided to the brake disc.
Figure 12:
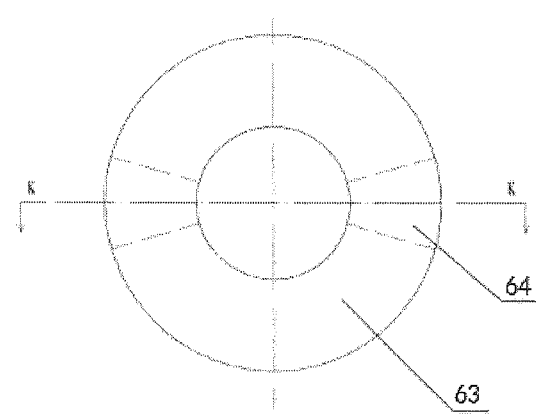
FIG. 12 is a plan view of the present invention.

As is depicted in FIGS. 10 and 11, the end part of the wind wheel shaft is provided with a brake disc II 88, an annular slot I 14 is provided on the brake disc II 88, and a rubber ring I 15 is arranged within the annular slot I 14. In the natural state, the rubber ring I 15 is in contact with the head covering 5, but in the working state the rubber ring I 15 separates from the head covering and enters into the slot due to centrifugal force. In this manner, the rubber ring I 15 also has both a braking function as well as a balancing function for automatically adjusting the wind wheel. Even more advantageously, a rubber membrane 19 can be assembled on the rubber ring I 15, increasing the frictional surface area and braking ability.

As is depicted in FIGS. 10 and 11, an annular slot II 16 is provided on a wind wheel blade 4 side of the wind wheel shaft 3, and a rubber ring II 17 is arranged within the annular slot II 16; in the natural state, the rubber ring II 17 is in contact with a bearing seat 18 of the head housing 1, but in the working state, the rubber ring II 17 separates from the bearing seat 18 and enters into the slot due to centrifugal force. The rubber ring I 15 also has both a braking function as well as a balancing function for automatically adjusting the wind wheel.

In FIGS. 10 and 11, the annular slots are provided both on the end part of the wind wheel shaft and on the wind wheel blade side, but in practice it would also be possible to have only one annular slot; it will be readily understood that it can be arranged on both sides of the wind wheel blade.

The mode described above is not limited to the head covering in the drawings where the bur is loaded and unloaded via a push button; a head covering where a key is used to load and unload the bur can similarly be implemented.

With respect to the heads where the bur is inserted or removed or where the bur is loaded and unloaded using a key, the brake pad 8 can be directly arranged on the end part of the wind wheel shaft, with the through hole provided to the center of the brake pad 8 being used for the insertion of an ejector pin or key; the drawings omit a depiction of such circumstances.

The drawings depict a head where the bur is loaded and unloaded using a push button, the wind wheel shaft 3 being provided with the clamping jaw hole and the clamping jaw 9 inside the clamping jaw hole being directly connected to the clamping jaw rod 10; the clamping jaw rod 10 extends out of the clamping jaw hole and is fixed at an end part to the spring retaining ring 24. In the drawings a disc spring is retained by the spring retaining ring 24; similarly a butterfly coil spring retained by the spring retaining ring is capable of being used; the spring retaining ring 24 is the end part of the wind wheel shaft 3. The increased diameter of the spring retaining ring is the brake disc 8, and the clamping jaw 9, the clamping jaw rod 10, and the spring retaining ring 24 integrally combine to serve as a clamping piece. The material of the wind wheel and the clamping piece can be plastic, or can be metal; costs are lower when metal die-casting is used. A disc spring is provided between the end of the wind wheel shaft and the spring retaining ring 24. During installation, the clamping jaw 9 is clasped and inserted into the conical clamping jaw hole, and the bur is inserted into the clamping jaw. With respect to the head where the bur is inserted or removed or where the bur is loaded and unloaded using a key, since no clamping piece is provided, the end part of the clamping jaw hole is thus equivalent to the end part of the wind wheel shaft.

The present invention is not limited to the embodiment described above; any scheme that is equivalent to the present invention and any technology described by the present invention fall under the scope of the present invention.

As is illustrated in FIGS. 12 to 15, the LED lamp of the present invention is annular, the upper surface thereof (meaning the back surface of the light-emitting surface) being an electrode. The upper surface of the annular LED lamp is provided with an electroconductive thin-film 63 supported by an insulator 64, where an LED lamp switch is constituted of contact between and separation of the electroconductive thin-film 63 and the upper surface of the annular LED lamp.

The above-described electroconductive thin-film 63 can be a metallic thin-film, or can be an electroconductive adhesive coated onto a non-metallic thin-film. When the electroconductive thin-film 63 is a metallic thin-film, the thin-film can be silver foil, copper foil, aluminum foil, or the like; when the electroconductive thin-film 63 is a non-metallic thin film, the thin-film can be an electroconductive polyester or polyvinylchloride. In the case of a polyester, polysulfide ester can be used.

Figure 13:
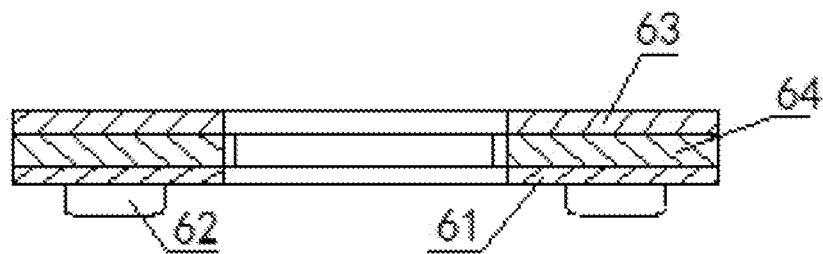
FIG. 13 is a cutaway view during illumination of the LED light source installed in the present invention, the cutaway view being along the K-K line in FIG. 1.

The above-described annular LED lamp can have a variety of different forms:

(1) The annular LED lamp refers to an LED lamp 62 provided on a bottom surface of an annular circuit board 61, the LED lamp 62 being a point light source; under such circumstances, the upper surface of the annular circuit board 61 is a copolar surface, as is illustrated in FIG. 13.

Figure 14:
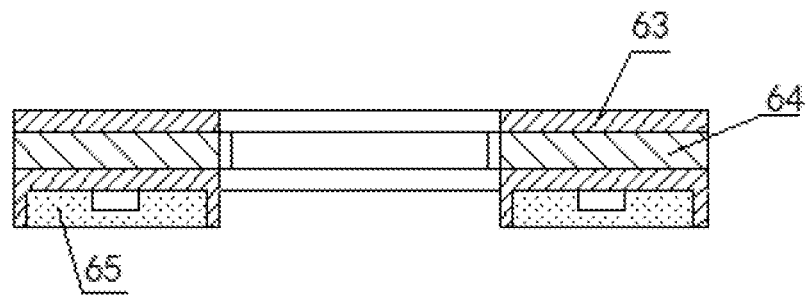
FIG. 14 is a cutaway view of when an annular LED lamp of the present invention is a COB surface light source, the cutaway view being along the K-K line in FIG. 1.

(2) The annular LED lamp is an annular COB surface light source 65, the upper surface of the annular COB light source 65 being copolar; an integrated LED light source is arranged in an annular manner below the upper surface of the COB light source and is encapsulated with a sealing compound. The sealing compound contains a phosphor powder, as is depicted in FIG. 14.

Figure 15:
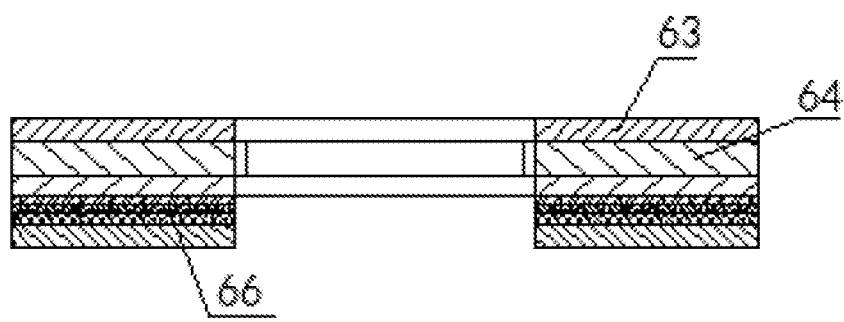
FIG. 15 is a cutaway view of when the annular LED lamp of the present invention is an OLED surface light source, the cutaway view being along the K-K line in FIG. 1.

(3) The annular LED lamp is an annular OLED surface light source 66, the upper surface of the annular OLED surface light source 66 being copolar; the upper surface of the annular OLED surface light source 66 is a negative electrode, and an electron transport layer, organic light-emitting layer, hole transport layer, and glass substrate are formed in the stated order therebelow. The glass substrate is a positive electrode, and the annular OLED surface light source is thus configured, as is illustrated in FIG. 15.

It must be stated that the above-described COB and OLED light emission are both prior art, but the annular shape of the COB and the OLED is distinct from the prior art.

The operating principle of the present invention is that the present invention will be arranged on an air outlet channel of a dental drill handpiece. When air is flowing, the electroconductive thin-film 63 and the annular LED lamp are in contact and the circuit is closed, thus causing the LED lamp to begin illuminating; when air flow ceases, the electroconductive thin-film 63 and the annular LED lamp are separated, and the circuit is broken, thus turning off the LED lamp.

Figure 16:
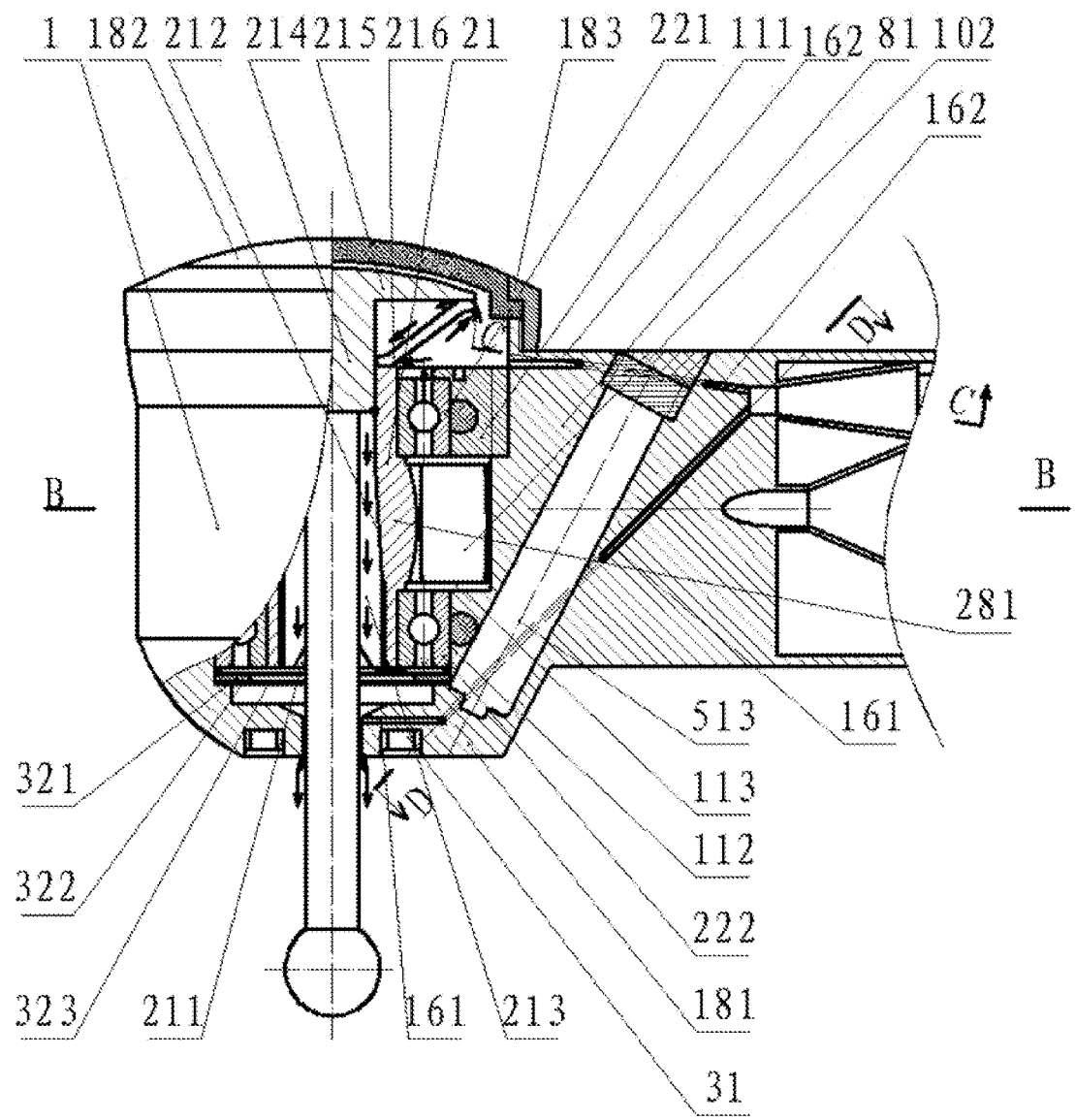
FIG. 16 is a cutaway schematic structural view of the head.
Figure 17:
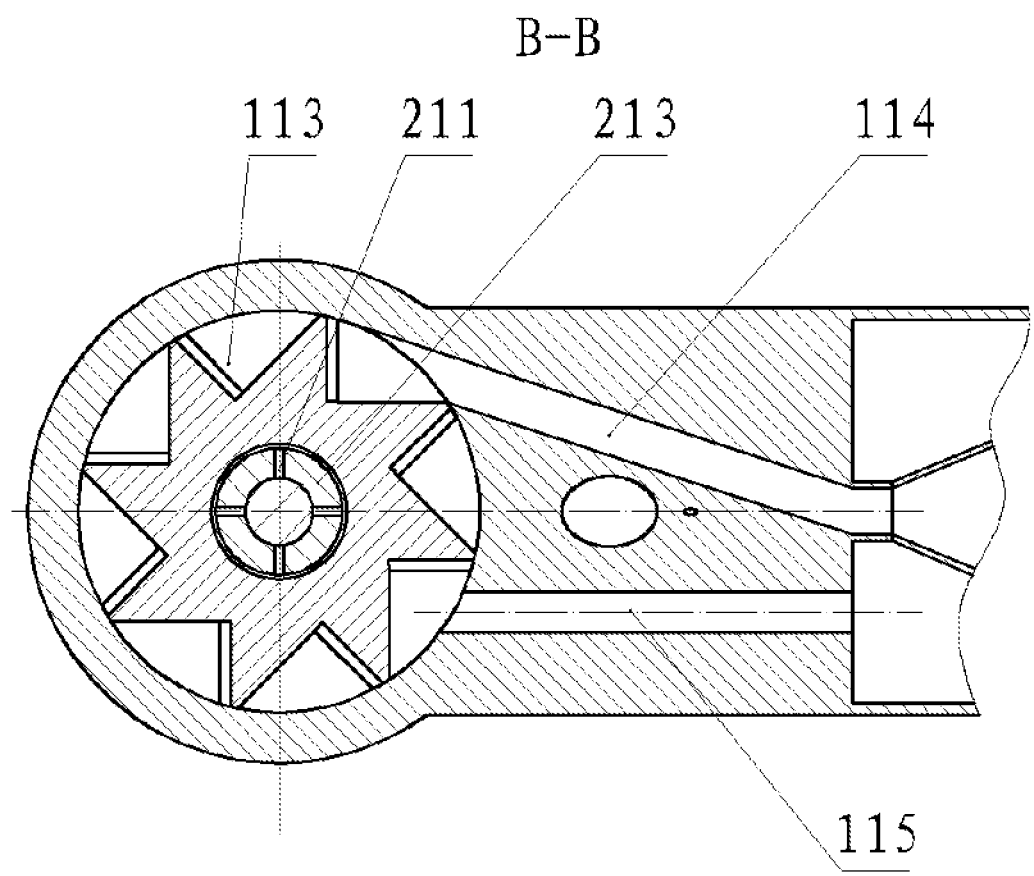
FIG. 17 is a cutaway schematic structural view along the B-B line in FIG. 15.

A dental turbine drill comprises a handle and a head that is connected to the handle; as is illustrated in FIG. 16, the head is constituted of a head housing 1 and a core 102 that is arranged within a cavity of the head housing; the head housing 1 is constituted of a head housing wall 181 and a head housing covering 182, while the core 102 is constituted of a connecting shaft turbine and an upper bearing 221 that is fitted at an upper site on a turbine shaft 281 of the connecting shaft turbine as well as a lower bearing 222 that is fitted at a lower site on the turbine shaft 281 of the connecting shaft turbine. The upper bearing 221 is placed on an upper bearing seat 111 inside the head housing, and the lower bearing 222 is placed on a lower bearing seat 112 inside the head housing. A turbine cavity 113 is formed between the upper bearing 221 and the lower bearing 222, and, as is illustrated in FIG. 17, the turbine cavity 113 is provided with an air supply channel 114 and an air return channel 115; the upper part of the upper bearing 221 is an upper air outlet channel and the lower part of the lower bearing 222 is a lower air outlet channel; the site of the connection between the handle and the head housing is a handle neck 81, and both the head housing and the handle are made of a plastic material.

As is illustrated in FIG. 16, an LED surface mount lamp 31 is arranged on the outer periphery of a bur socket on the outside of the head housing wall 181, and the LED surface mount lamp 31 is connected to a power source and a switch, the switch referring to a pneumatic membrane switch provided on the lower air outlet channel.

Figure 18:
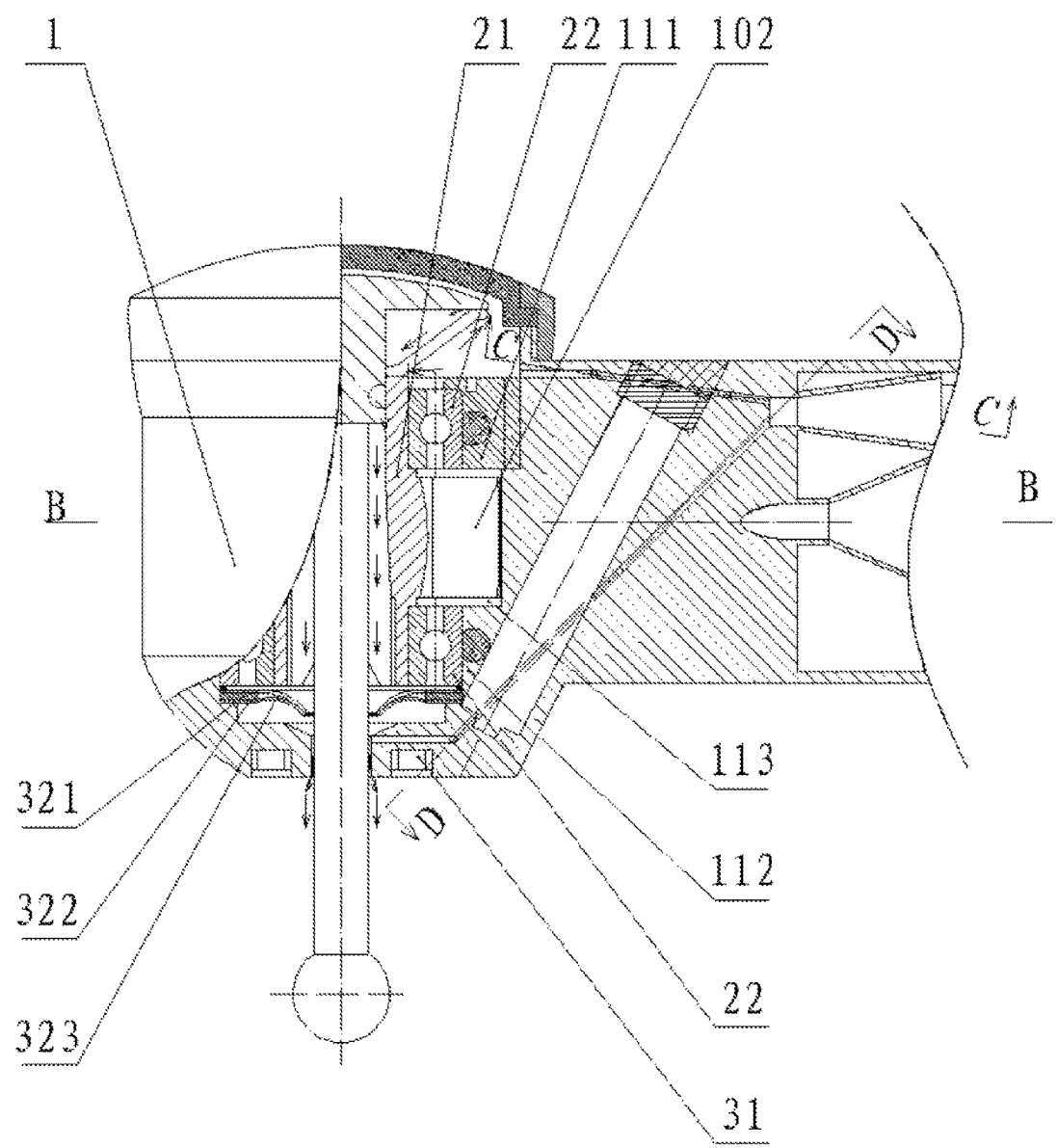
FIG. 18 is a cutaway schematic structural view of when the blades are in contact with the head.

The pneumatic membrane switch is constituted of two membrane rings 322 that are isolated from an annular isolation layer I 321 by a distance that corresponds to the annular isolation layer I 321, projecting blades 323 being arranged in the direction of the ring center of the two-membrane rings, where the pneumatic membrane switch is configured to open and close by the contact in FIG. 18 and separation in FIG. 16 between the two corresponding projecting blades 323.

Figure 19:
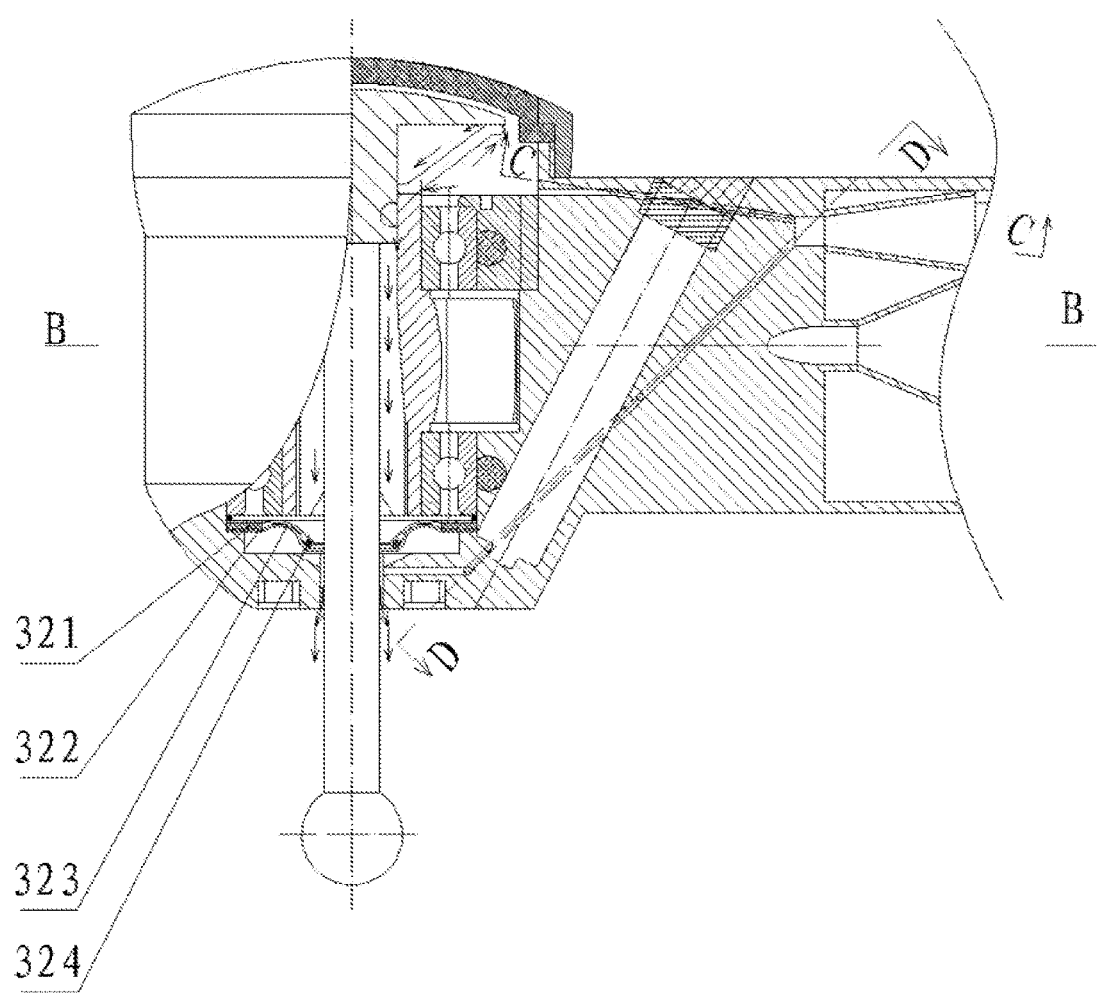
FIG. 19 is a cutaway schematic structural view of when an isolating blade provided to the blade tip is in contact with the head.
Figure 20:
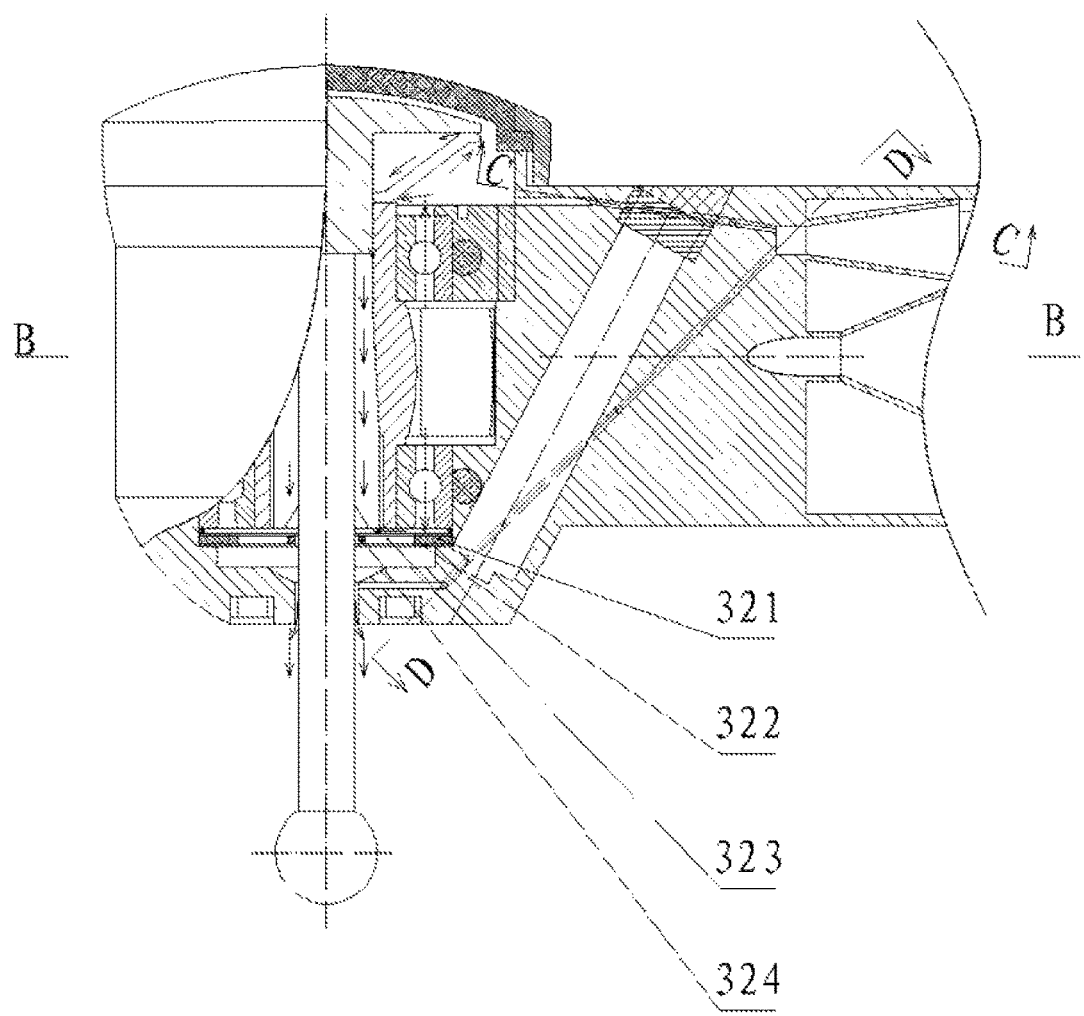
FIG. 20 is a cutaway schematic structural view of when an isolating blade provided to the blade tip separates from the head.

As is illustrated in FIG. 19, the two projecting blades 323 approach the extremity of the ring center fixed to the isolation layer II 324. The two projecting blades 323 do not make contact with the isolation part as in FIG. 19, but are separated as in FIG. 20 to constitute the opening and closing of the pneumatic membrane switch.

Figure 21:
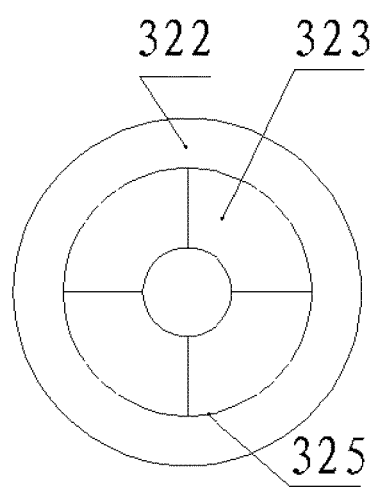
FIG. 21 is a schematic view of a T-shaped slit.

As is illustrated in FIG. 21, the ring width of the two membrane rings isolated from the annular isolation layer I 321 is greater than the ring width of the annular isolation layer I 321, and a T-shaped slit is provided toward the ring center direction along the inside of the annular isolation layer I 321 on the two membrane rings. The projecting blades 323 are configured between the two neighboring T-shaped slits 325. The site to which the annular isolation layer corresponds is the membrane ring 322.

Figure 22:
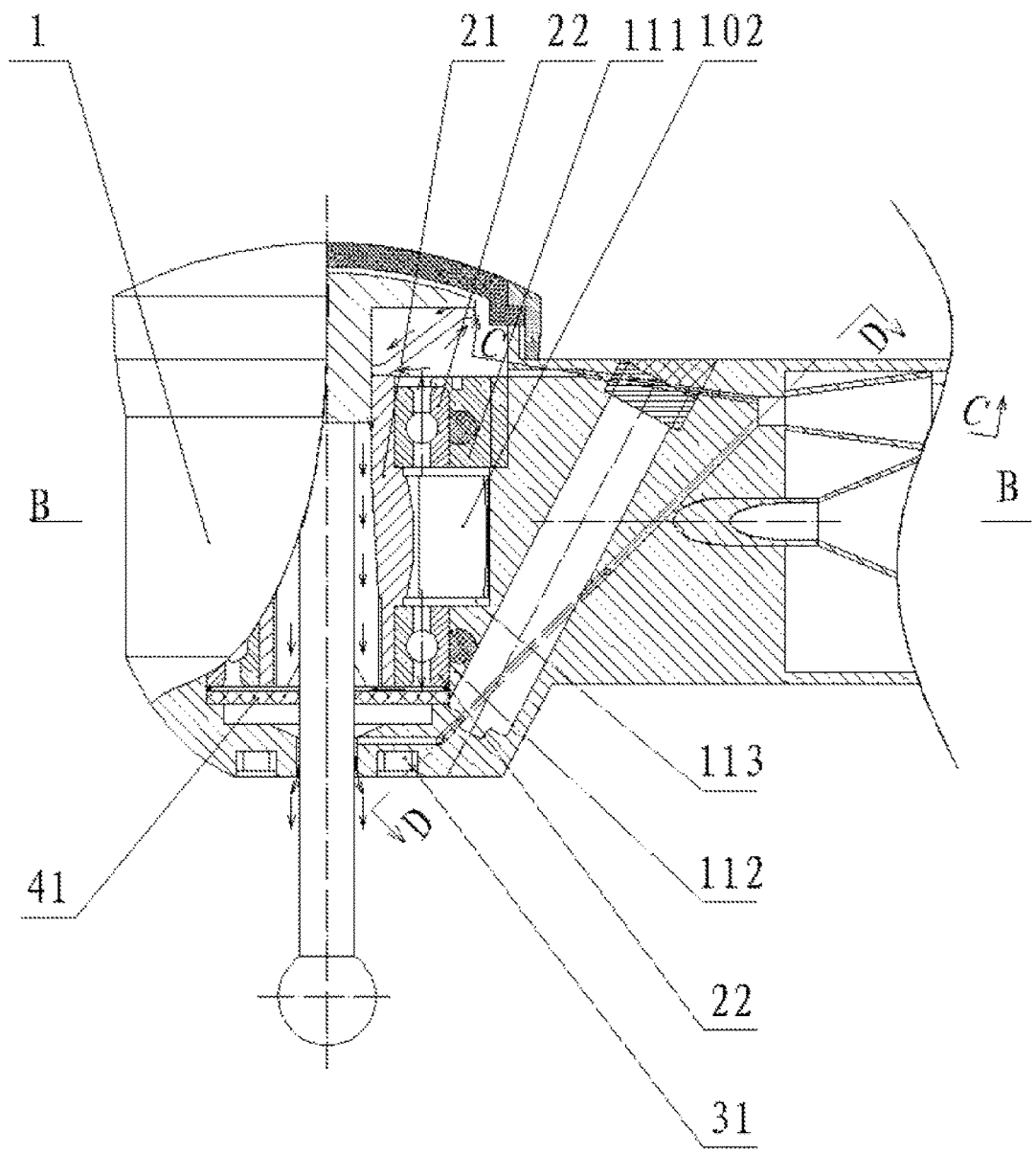
FIG. 22 is a cutaway schematic structural view of the head when an annular stretched elastic membrane is fixed onto the air outlet channel.
Figure 23:
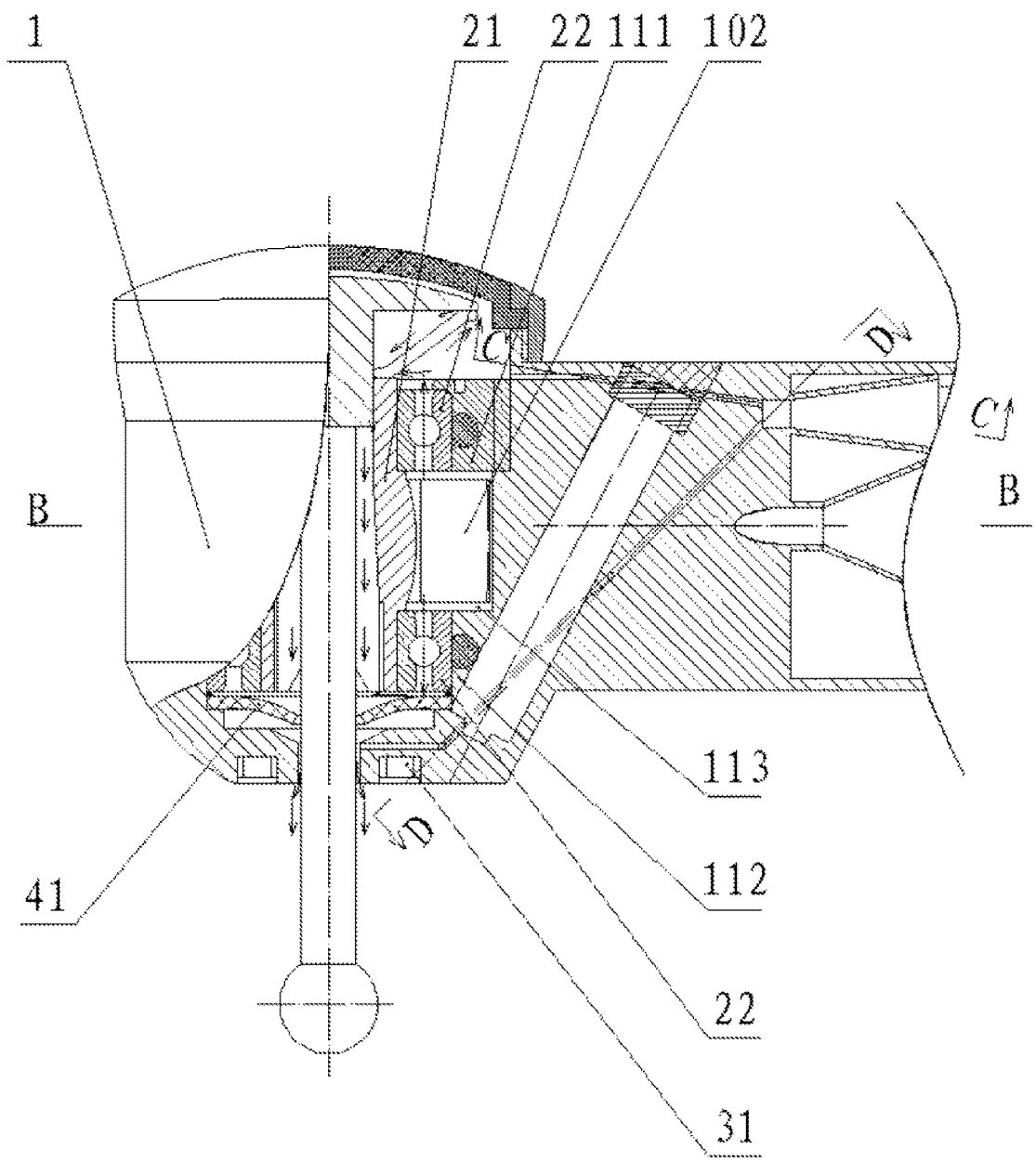
FIG. 23 is a cutaway schematic structural view of the head when the annular stretched elastic membrane fixed onto the air outlet channel is blown open.

In the above-described dental turbine drill, an annular one-way valve is fixed onto the air outlet channels; as illustrated in FIG. 22, the annular one-way valve is an annular stretched elastic membrane 41. In the natural state, a center hole of the annular stretched elastic membrane 41 holds onto the bur, the depiction showing only the holding of the bur, but the turbine shaft can also be lengthened to allow the center hole to hold onto the turbine shaft. In the working state, as illustrated in FIG. 23, the center hole of the annular stretched elastic membrane is blown away from the bur, but it will be readily understood that the center may also be blown away from the turbine shaft.

The annular stretched elastic membrane 41 is a soft silicone rubber, polyurethane, latex, or ordinary rubber.

The thickness of the annular stretched elastic membrane 41 is approximately several tens of micrometers to two millimeters.

Figure 24:
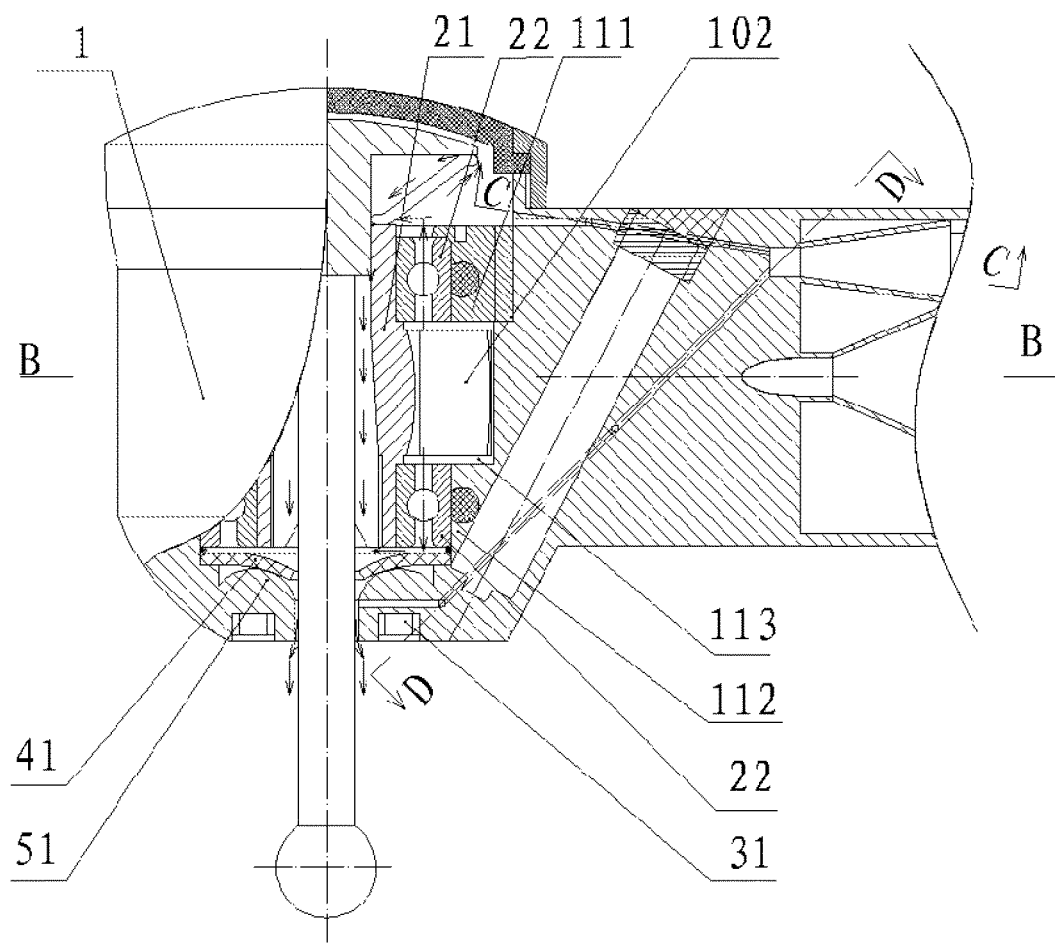
FIG. 24 is a cutaway schematic structural view of the head when the annular stretched elastic membrane is in contact with the upper surface of an LED lamp stand.

In the natural state, a portion of the lower surface of the annular stretched elastic membrane 41 is separated from the upper surface of the head LED lamp seat 51, and in an air expelling state, as is illustrated in FIG. 24, that portion is in contact with the upper surface of the head LED lamp seat 51, whereby the site of contact between the upper surface of the head LED lamp seat 51 and that portion of the lower surface of the annular stretched elastic membrane 41 constitutes a switch. Under such circumstances, the annular stretched elastic membrane is a conductor, and the upper surface of the LED lamp seat is a conductor.

Figure 25:
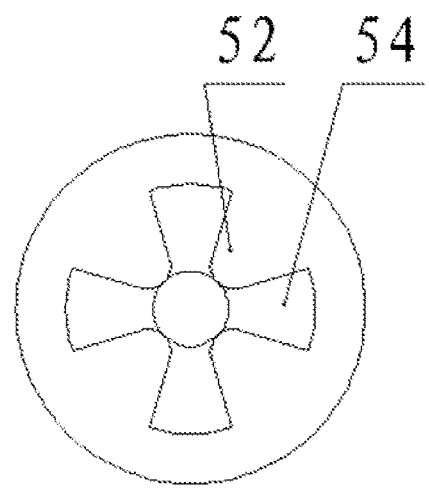
FIG. 25 is a view of a lower surface of the annular stretched elastic membrane.

A conductor 52 is arranged on the lower surface of the annular stretched elastic membrane. FIG. 25 is a view of the lower surface of the annular stretched elastic membrane, where the conductor 52 is distributed radially toward the center and has an annular connection to the outer peripheral edge of the annular stretched elastic membrane 41. A conductor is arranged at an upper surface site of the LED lamp seat inside the head. The annular stretched elastic membrane at the site to which the conductor 52 corresponds is thicker, and forms a convexity, while the site where the conductor 52 is not arranged is thinner, and forms a recess 54.

Figure 26:
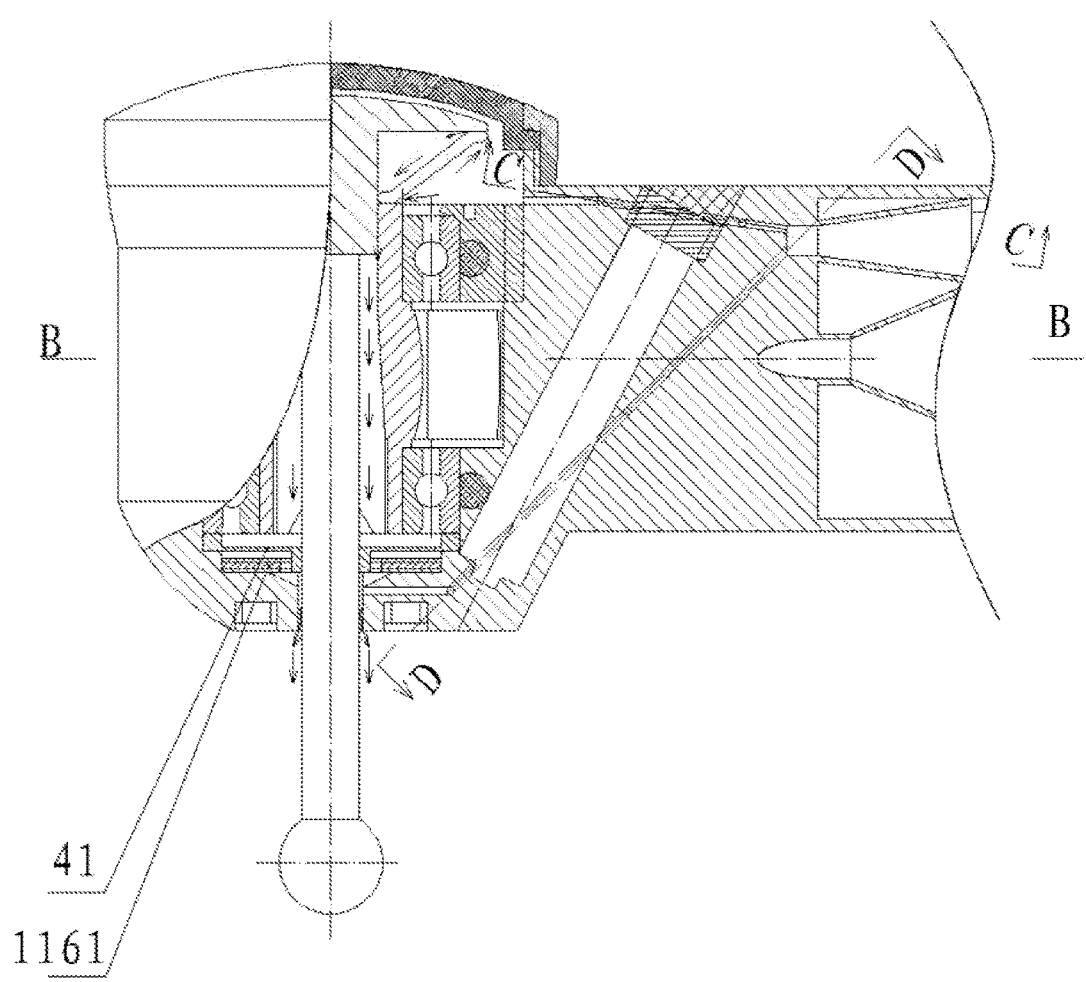
FIG. 26 is a cutaway schematic structural view of the head when an annular pressure membrane switch is arranged below the annular stretched elastic membrane.

As is illustrated in FIG. 26, an annular pressure membrane switch 1161 is arranged below the annular stretched elastic membrane 41.

Figure 27:
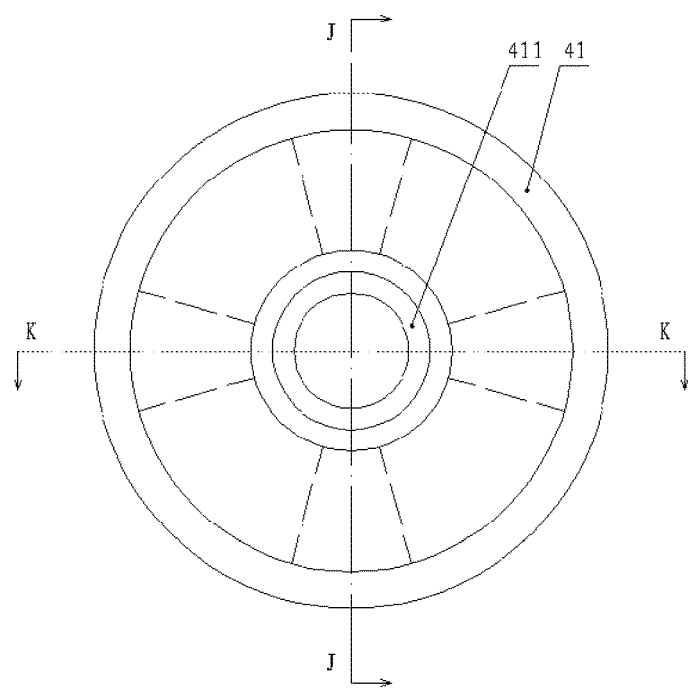
FIG. 27 is an enlarged schematic view of when the annular pressure membrane switch is provided below the annular stretched elastic membrane.
Figure 28:
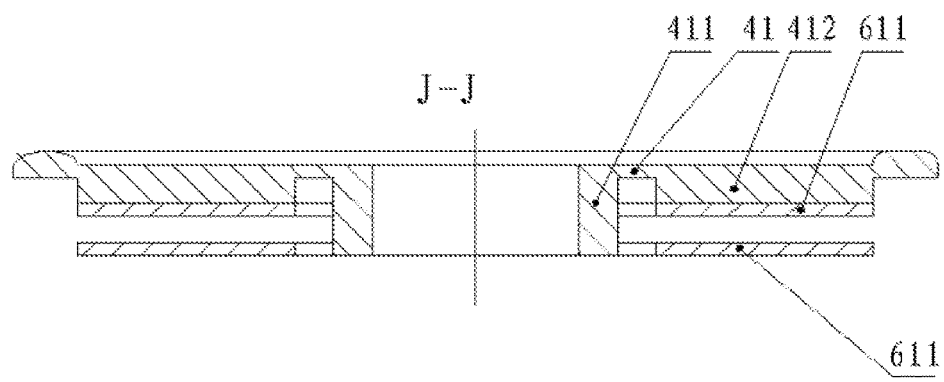
FIG. 28 is a cutaway schematic structural view along the J-J line in FIG. 27.
Figure 29:
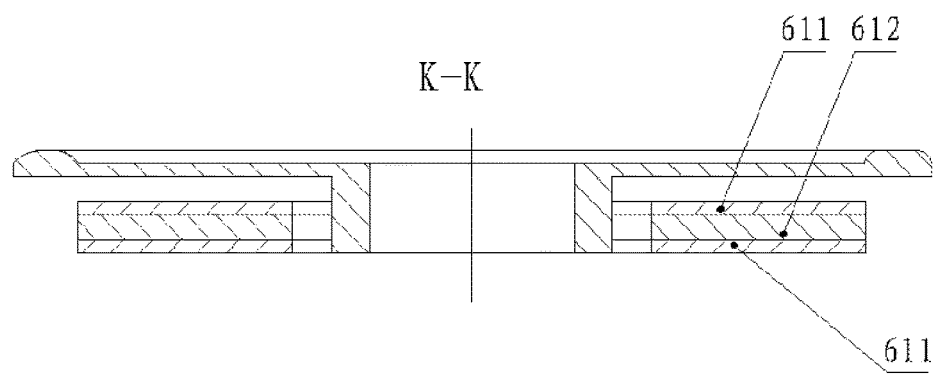
FIG. 29 is a cutaway schematic structural view along the K-K line in FIG. 27.

As is illustrated in FIGS. 27 to 29, the annular pressure membrane switch refers to two isolation points 612 arranged between the upper and lower membrane rings 611; the sites of the membrane rings 611 where there is no isolation point 612 contact each other when subjected to pressure but are separated in the natural state, thus constituting the pressure membrane switch.

As is illustrated in FIG. 28, the elastic membrane 611 is thicker around the periphery of the center hole, thus forming an annular stand ring 411. A pressure block 412 thinner than the annular stand is arranged on the outside of the annular stand ring 411, and a top part connects the annular stand ring and the pressure block. The pressure block 412 corresponds to a site of the annular membrane switch where no isolation point is arranged. During operation, the airflow pressure applies pressure to the pressure block 512, causing the two elastic rings to come into contact and complete the circuit; when operation is stopped, the pressure block 412 lifts up automatically, thereby separating the two elastic rings 611 and opening the switch.

As is illustrated in FIG. 16, the LED lamp and switch are arranged on a site on the head, and at least a portion of a power source assembly is arranged on a site on the head. Reducing the path link between components makes it possible to simplify the manufacturing process and reduce the number of disposable components.

Figure 30:
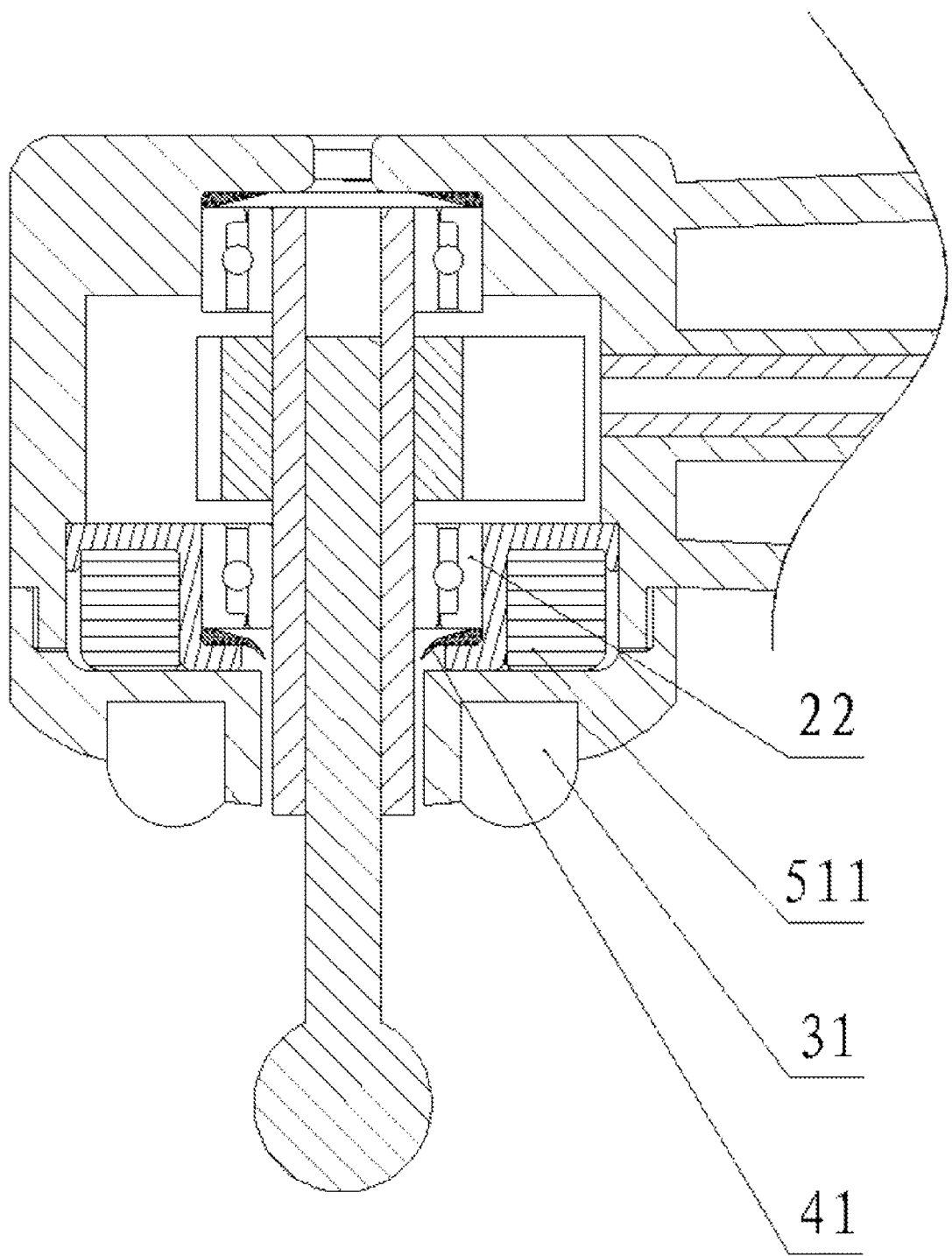
FIG. 30 is a schematic view of an annular battery provided within the head.

An annular battery 511 power source arranged inside the head is illustrated in FIG. 30.

Figure 31:
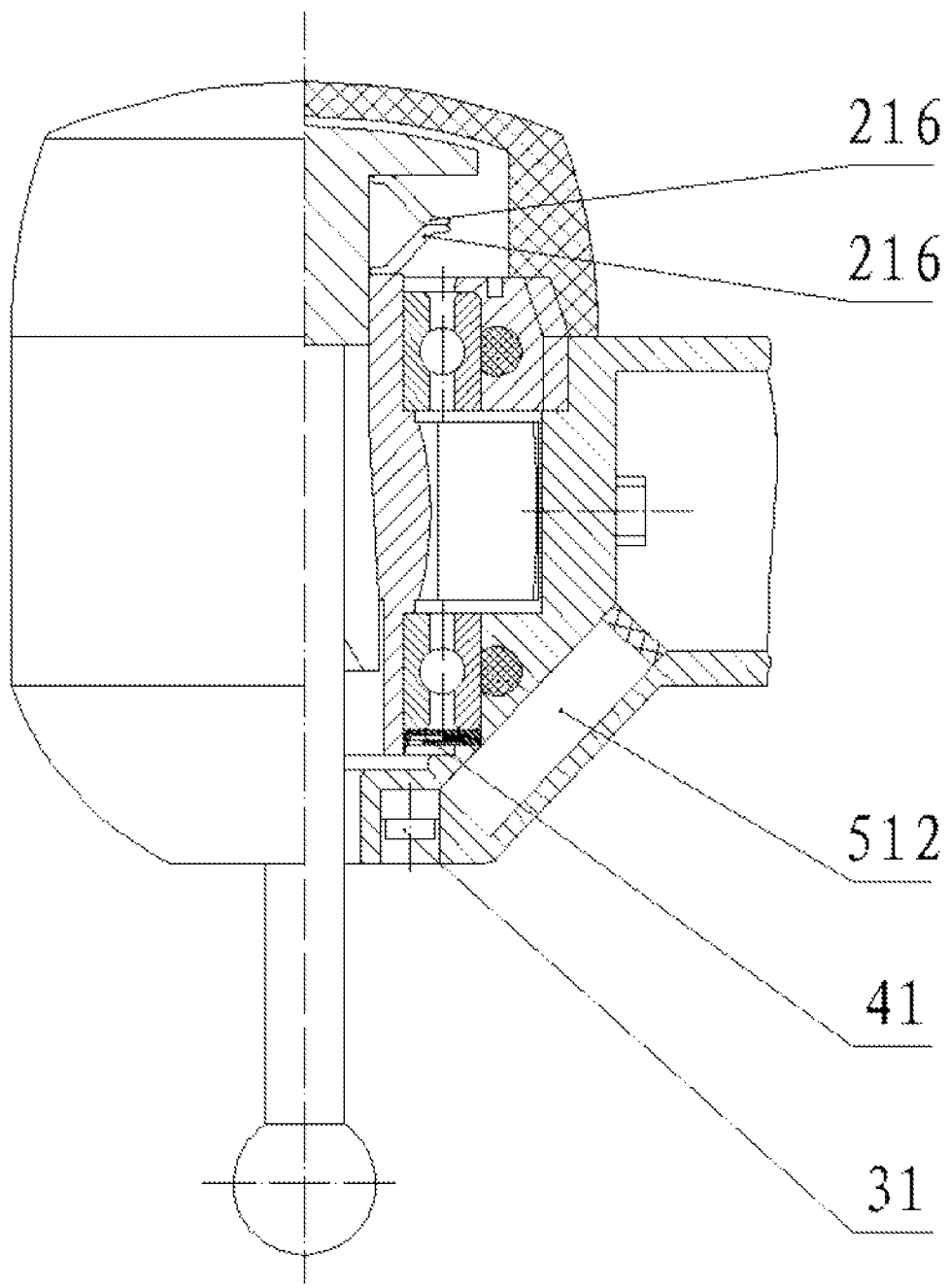
FIG. 31 is a cutaway schematic structural view of the head when a button battery is arranged in the neck part of the head.

A Sony 337 button battery 512 power source arranged on one side of the neck part of the head is illustrated in FIG. 31.

A pin type battery 513 power source arranged on one side of the neck part of the head is illustrated in FIG. 16. A No. 208 pin type battery is also called a fishing float battery; the No. 208 has a diameter of 2 mm and a length of 8 mm.

As is illustrated in FIG. 16, the turbine drill is a push button dental drill, and the material of the head covering 182 is a rubber-like substance. The rubber-like substance of the head covering is tightly clamped by a clamp 183 on an upper part of the head housing wall 181. The upper bearing seat 11 is screwed into the cavity formed inside the head housing wall 181.

The rubber-like substance of the head covering is a silicone rubber, polyurethane, latex or ordinary rubber.

The dental turbine drill, as is illustrated in FIG. 16, is a push button turbine drill, and a bur pressure clamping mechanism thereof is a tapered hole 212 arranged in the center hole 211 of the turbine shaft 281, a clamping jaw 213 being provided within the center hole 212 of the turbine shaft; along the axial direction of the clamping jaw 213 along the turbine shaft is a wedge shape that is mated to the tapered hole, and an upper part of the clamping jaw 213 and a connecting rod 214 are integrally fixed together. A spring retaining board 215 and the center hole 211 of the turbine shaft, which extends out from the upper part of the connecting rod 214, are integrally fixed together, and a spring 216 is provided between the turbine shaft 281 and the spring retaining board 215 on the outside of the connecting rod 214.

The turbine shaft 281, the clamping jaw 213, the connecting rod 214, and the spring retaining board 215 are all plastic pieces. The clamping jaw acts similarly to a conventional spring valve of a three-piece spring for a dental drill, and an advantage of having plastic pieces is that the plastic pieces are less rigid and the shape of the plastic pieces will be modified after being subjected to pressure; this modification will increase the contact surface area and the frictional force between the bur, the wedge, the wind wheel shaft, and the three inner holes. If the wedge breaks, the bur is less prone to fly off.

The spring retaining board 215 is an inertia plate. The inertia plate has a greater diameter than a conventional spring retaining board; by increasing the size of the inertia plate, there is more moment of inertia during rotation; when cutting, a considerable rotational speed can still be retained, and the rotational speed remains stable.

The spring is a butterfly spring or a leaf spring. The butterfly spring and leaf spring both increase the moment of inertia equally.

As is illustrated in FIG. 31, the butterfly spring or leaf spring is arranged so as to snap into relative superposition, and this manner of arrangement increases the pressing stroke.

Figure 32:
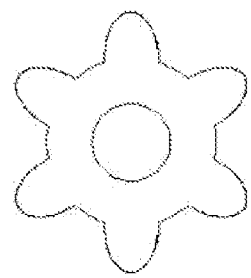
FIG. 32 is an external view of a grooved butterfly spring.
Figure 33:
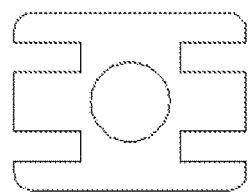
FIG. 33 is an external view of a grooved leaf spring.

The butterfly spring, as is illustrated in FIG. 32, is a grooved butterfly spring, and the leaf spring, as is illustrated in FIG. 33, is a grooved leaf spring.

When the clamping jaw has clamped onto the bur, an upper end of the center hole of the turbine shaft communicates to the lower end thereof. The communication between the upper end and lower end of the center hole of the turbine shaft means that air flowing from the upper end of the turbine shaft center hole will be able to flow through to the lower end. In such circumstances, when the bur is clamped, there can be communication through the gap between the components as long as the tapered hole portion of the turbine shaft is not sealed.

Figure 34:
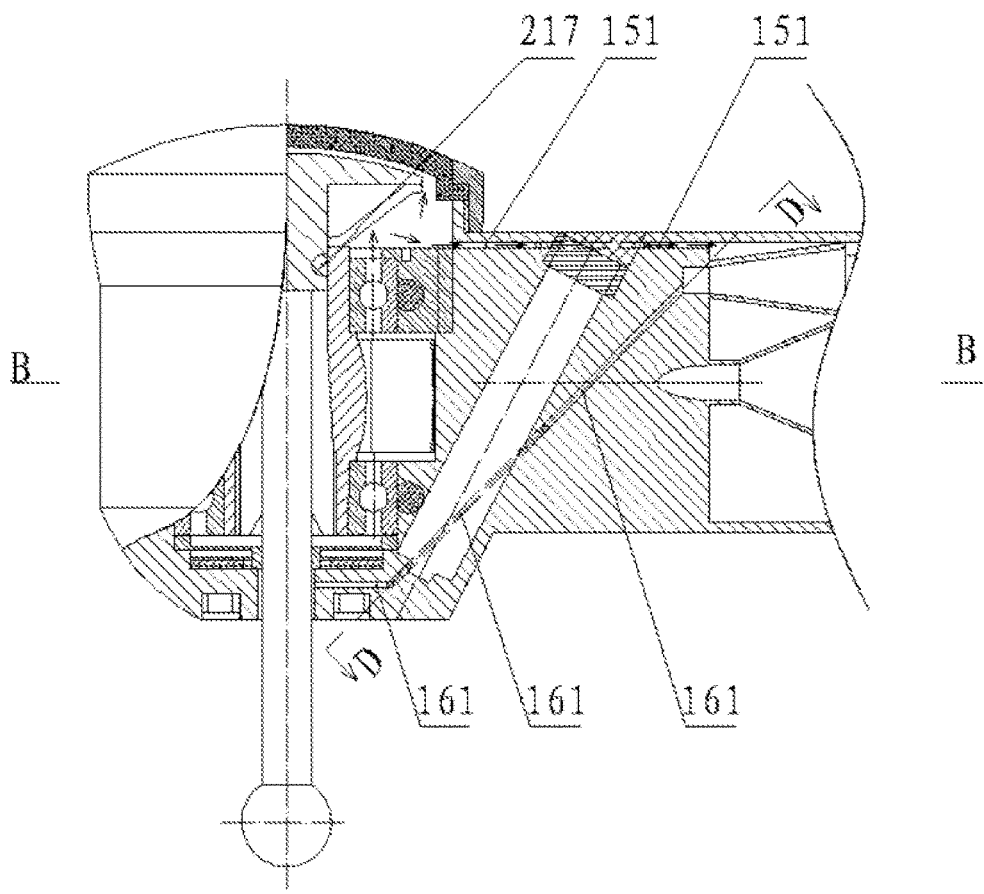
FIG. 34 is a cutaway schematic structural view of the head when a sealing ring arranged between a connecting rod and a center hole of the turbine shaft is also arranged with a return air channel II.
Figure 35:
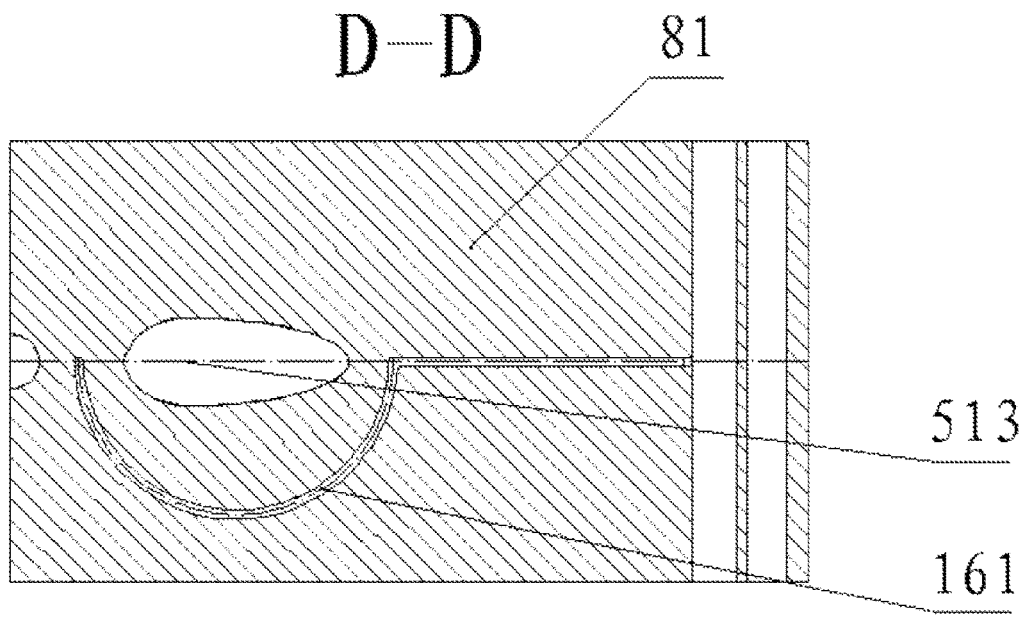
FIG. 35 is a cutaway schematic structural view along the D-D line in FIG. 16.
Figure 36:
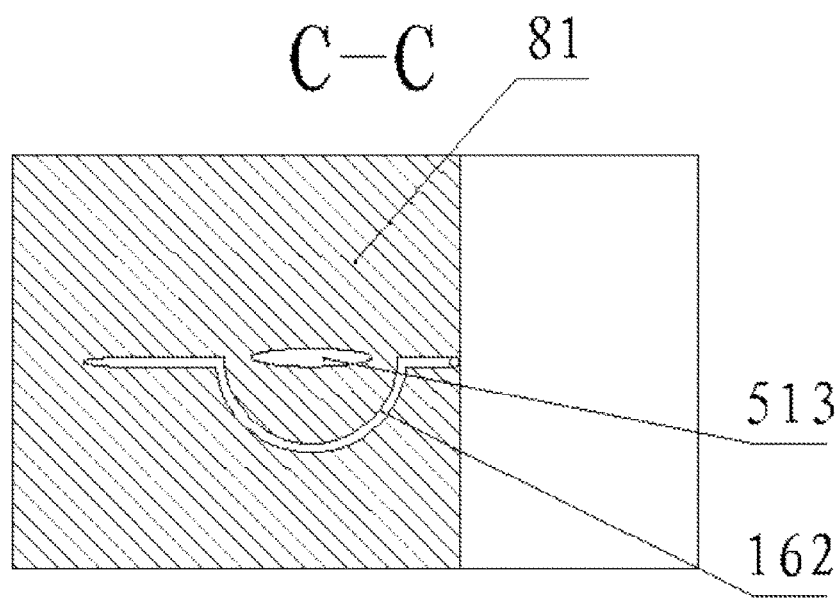
FIG. 36 is a cutaway schematic structural view along the C-C line in FIG. 16.
Figure 37:
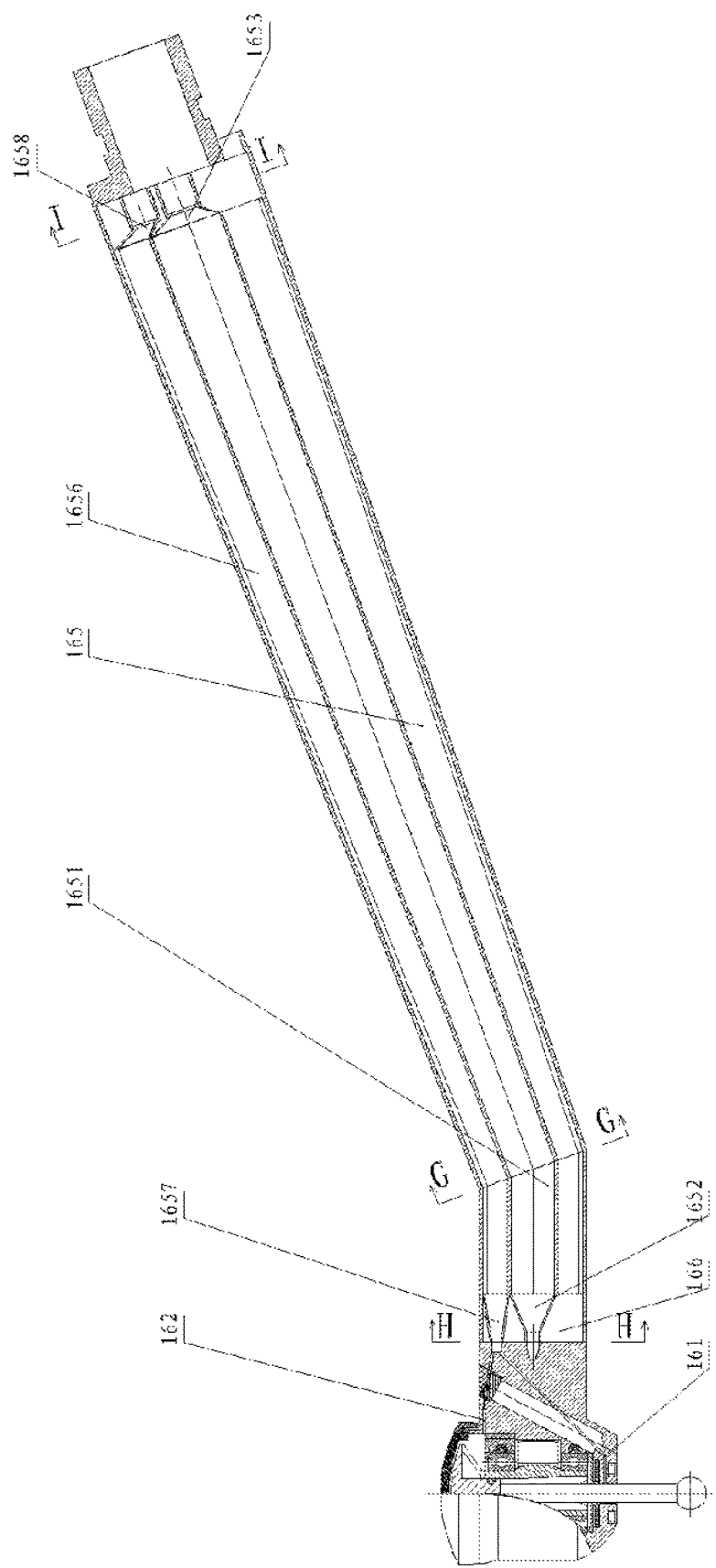
FIG. 37 is a cutaway schematic structural view of the entirety.
Figure 38:
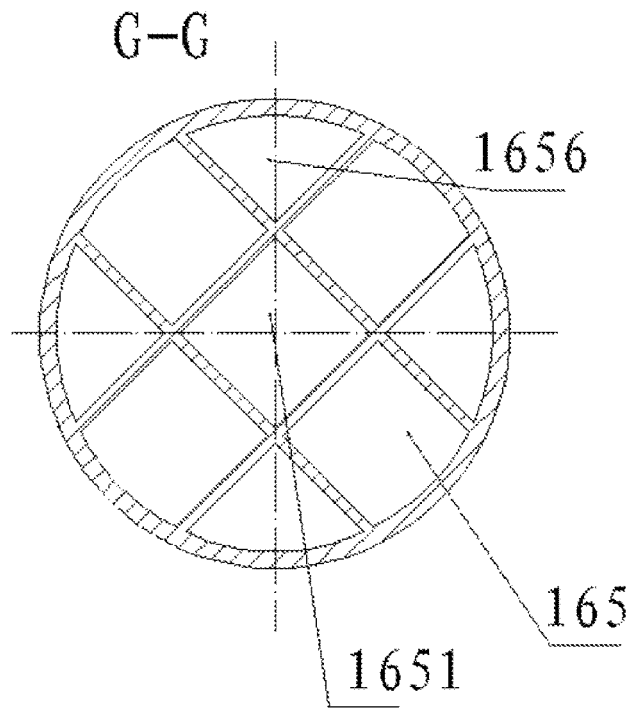
FIG. 38 is a cutaway schematic structural view along the G-G line in FIG. 37.
Figure 39:
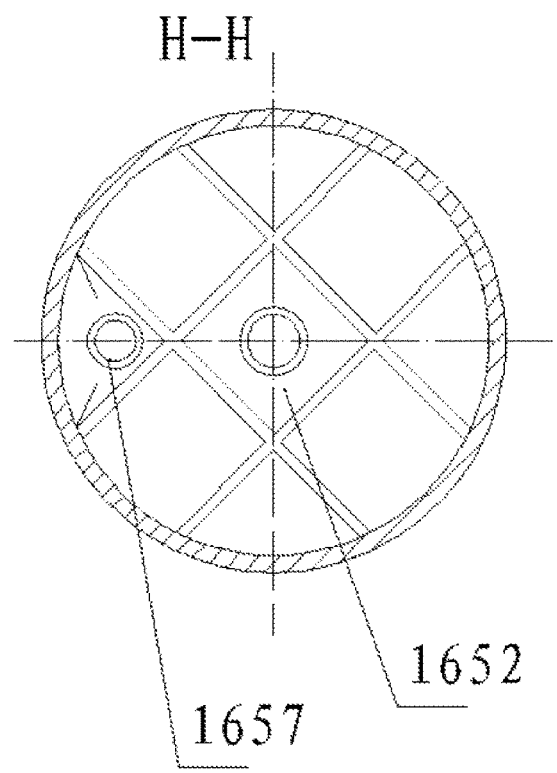
FIG. 39 is a cutaway schematic structural view along the H-H line in FIG. 37.
Figure 40:
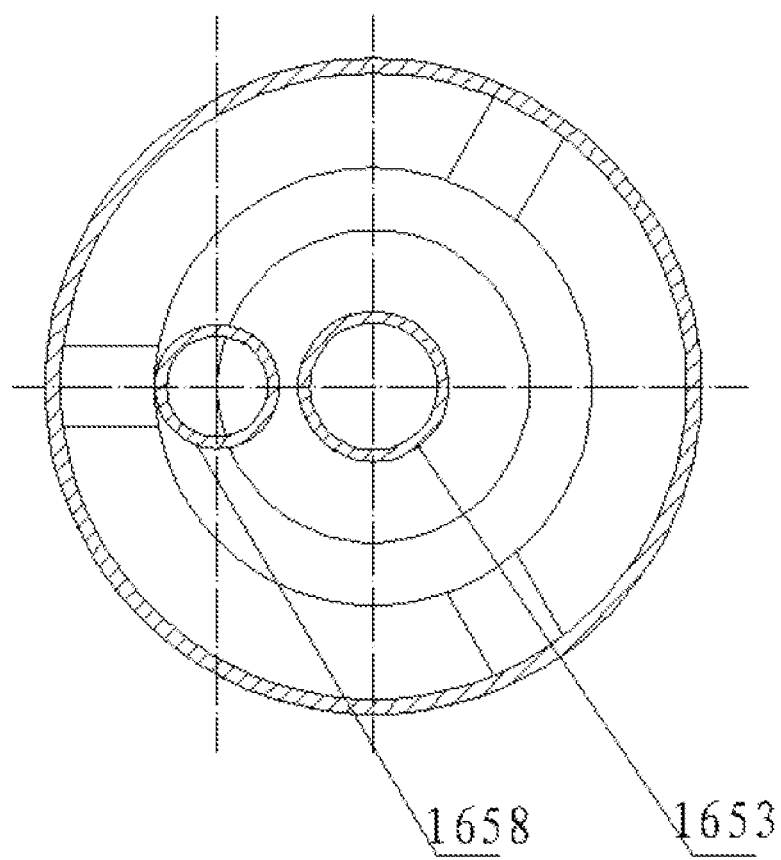
FIG. 40 is a cutaway schematic structural view along the I-I line in FIG. 37.

In the dental turbine drill, as is illustrated in FIG. 34, a sealing ring 217 is arranged between the connecting rod and the turbine shaft center hole. A return air channel II 151 that communicates with the return air channel is arranged on the upper air outlet channel. (The reason for arranging the return air channel II such that the return air channel II communicates with the return air channel at the neck part is to lower the temperature of the bearings.) In the present embodiment, the return air channel II enters into the handle, and there is a space on the outside of an air inlet channel pipe and a water ejection channel pipe. The return air channel also enters into this space.

As is illustrated in FIG. 34, a lower water ejection hole 161 is arranged on the lower air outlet channel.

As is illustrated in FIG. 16, an upper water ejection hole 162 and a lower water ejection hole 161 are arranged on the upper and lower air outlet channels; it would also be possible to arrange only the upper water ejection hole 162. The water ejected from the water ejection holes of the lower air outlet channel is atomized by the airflow ejected from the cavity, and is discharged in tandem with the rotation of the turbine shaft or the bur. This makes adequate atomization and cooling of the bur possible. At the same time, there is no dedicated air ejection channel for atomizing water vapor, and since conventional dedicated channels for atomizing water vapor are in communication with an air supply channel supplied by the rotation of the turbine, forgoing the dedicated air ejection channel for atomizing the water vapor makes it possible to avoid suck-back into the air ejection channel; moreover, with the water ejection hole on the upper air outlet channel, since the upper covering is sealed, water and air will flow via the gap between the butterfly spring or leaf spring and the turbine shaft and inertia plate, entering into the gap between the connecting rod and the hole inside the turbine shaft, and then passing through the gap between the wedge to enter into the lower air outlet channel and leave the head. During the described process, the water will be fully atomized. Under such circumstances, the amount of water ejected can be increased, and having the water pass through the gap between the internal components of the center hole of the turbine shaft makes it possible to eject water onto the bur.

As is illustrated in FIGS. 16, 34, 35, and 36, the upper water ejection hole 162 and the lower water ejection hole 161 are arranged on the inside of the head housing and on the neck of the handle. Situating the water ejection channel on the inside of the head housing wall can be achieved through the use of three-dimensional molding equipment. This embodiment is on the inside of the pipe wall, but in a conventional three-point atomization or multi-point atomization dental drill, an annular channel is arranged below the lower shaft bearing seat, the annular channel communicating with the water ejection channel and a dedicated air ejection channel for atomizing water; thus after water and air have been atomized in the annular channel, the atomized water will be ejected from a spray port arranged on the periphery of the bur. In the described structure, the dedicated water ejection channel for atomization is extraneous, and when the channel is not provided, the water will be discharged via the spray port and, since high-speed air is sprayed out of the lower air outlet channel, a negative pressure will be formed around the periphery of the bur. The negative pressure causes water to be sucked into the high-speed airflow, and the water is then naturally atomized. This scheme makes use of the airflow of the lower air outlet channel, and similarly is within the scope of protection of the present patent, and is an embodiment of the present invention; having the water of the annular channel directly enter into the lower air outlet channel is also an embodiment of the present invention.

In the dental turbine drill, as is illustrated in FIGS. 37 to 40, within the handle are grid channels 165 arranged along the axial direction of the handle; the grid channels 165 communicate individually with the head and with channels corresponding to the handle plug. Arranging the grid channels within the handle not only provides a supportive function, but also provides passages within the handle. With similar cross-sectional areas and similar numbers of passages, the utilization of the grid channels is highest, as the cross-sectional area of each grid channel is at a maximum. Further, a large number of channels can be arranged, and channels can be reserved for increasing the capabilities of the dental drill. A grid channel 1651 is an air inlet channel, and an air inlet pipe channel 1652 extending from the grid channel 1651 at the neck part of the handle communicates, as is illustrated in FIG. 17, with the air inlet channel 114 of the head, while an air inlet pipe channel 1652 extending from the tail part of the handle communicates with the air inlet channel of the handle plug. A grid channel 1656 is a water inlet channel, and a water inlet pipe channel 1657 extending from the grid channel 1651 at the neck part of the handle communicates, as is illustrated in FIG. 16, with the water inlet holes 161, 162 of the head, while a water inlet pipe channel 1658 extending from the tail part of the handle communicates with the water inlet channel of the handle plug. The return air channel 15 of the head communicates with the other grid channels via the cavity 166 inside the handle at the neck part, and these grid channels communicate with the return air channel of the plug via the cavity 167 inside the handle at the tail part. The air inlet pipe channel extending from the neck part of the handle from the grid channels communicates with the air inlet channel of the head; the air inlet pipe channel extends from the grid channels, and its shape corresponds to the shape of the grid channels. The shapes of the air inlet pipe channel and the air inlet channel of the head match at their site of communication. For example, if the grid channel is diamond-shaped, and the air inlet channel is round; then, the shape of the air inlet pipe channel will gradually change from diamond-shaped to round.

The invention claimed is:

1. A dental drill head, comprising:
    a head housing defining a head housing cavity, the head housing including a head covering enclosing an end of the head housing cavity, a periphery of the head covering being fixed onto the end of the head housing, the head covering being made of rubber, the head covering including an opening therein;
    a wind wheel including a wind wheel shaft and a plurality of wind wheel blades, the wind wheel being provided in the head housing, the wind wheel shaft including a first end point and a second end point opposite to the first end point in a longitudinal axis of the wind wheel shaft, wherein the first end point is located closer to the head covering than the second end point;
    a brake disc covering the first end point of the wind wheel shaft, the brake disc having a first end surface and a second end surface, the first end surface being positioned closer to the head covering than the second end surface; and
    an anti-suck-back device that is spaced apart from the first end point of the wind wheel shaft on the longitudinal axis of the wind wheel shaft, and between the head covering and the first end surface of the brake disc along the longitudinal axis of the wind wheel shaft, wherein the anti-suck-back device is positioned and configured to selectively block and unblock the opening in the head covering.

2. The dental drill head as set forth in claim 1, wherein the dental drill head further comprising a bur clamping mechanism arranged inside a hole of the wind wheel shaft,
    the bur clamping mechanism comprising:
        a clamping jaw positioned inside the hole of the wind wheel shaft,
        a clamping jaw rod, a first end of the clamping jaw rod being connected to the clamping jaw, and the brake disc being connected to a second end of the clamping jaw rod, and
        a spring being fitted onto the clamping jaw rod between the brake disc and a neck part of the wind wheel shaft.

3. The dental drill head as set forth in claim 2, wherein the clamping jaw rod has a sliding key fit with the hole of the wind wheel shaft.

4. The dental drill head as set forth in claim 1, wherein the anti-suck-back device is made of rubber,
    wherein in a natural state, the anti-such-back device is in contact with both the head covering and the brake disc, while in a working state, the anti-such-back device is separated from either the head covering or the brake disc.

5. The dental drill head as set forth in claim 4, wherein a first annular slot is provided on the brake disc, and the anti-suck-back device is a first rubber ring arranged within the first annular slot, wherein in the natural state, the first rubber ring is in contact with the head covering, but in the working state the first rubber ring separates from the head covering and enters the first annular slot due to inertia.

6. The dental drill head as set forth in claim 5, wherein a rubber membrane is provided on the first rubber ring.

7. The dental drill head as set forth in claim 4, wherein a second annular slot is provided adjacent to the wind wheel blades, and a second rubber ring is arranged within the second annular slot, wherein in the natural state, the second rubber ring is in contact with a bearing seat of the head housing that is located outside of the second annular slot, but in the working state, the second rubber ring separates from the bearing seat and enters the second annular slot due to inertia.

8. The dental drill head as set forth in claim 4, wherein the first end surface of the brake disc follows a shape of a surface of the anti-suck-back device that is in contact with the first end surface of the brake disc when in the natural state.

* * * * *